United States Patent [19]

DiNinno et al.

[11] Patent Number: 4,675,317

[45] Date of Patent: Jun. 23, 1987

[54] 2-UNSATURATED ALKYLTHIO-PEN-2-EM-3-CARBOXYLIC ACIDS

[75] Inventors: Frank P. DiNinno, Old Bridge; William J. Leanza, Berkeley Heights; Ronald W. Ratcliffe, Matawan; David A. Muthard, Rahway, all of N.J.

[73] Assignee: Merck & Co., Inc., Rahway, N.J.

[21] Appl. No.: 460,728

[22] Filed: Jan. 25, 1983

[51] Int. Cl.[4] .................. C07D 499/00; A61K 31/425
[52] U.S. Cl. .................................... 514/192; 540/310; 540/350; 514/194; 514/195
[58] Field of Search .................. 260/245.2 R, 245.2 T; 424/270; 514/192, 194, 195; 540/310

[56] References Cited

U.S. PATENT DOCUMENTS 4,168,314 9/1979 Christensen et al. ............... 424/270
4,395,418 7/1983 Ohki et al. .................... 260/245.2 R
4,517,124 5/1985 Brown .......................... 260/245.2 T

FOREIGN PATENT DOCUMENTS 0046363 2/1982 European Pat. Off. .
2042514 9/1980 United Kingdom .
2042520A 9/1980 United Kingdom .
2074563A 11/1981 United Kingdom .

OTHER PUBLICATIONS

J. Org. Chem. 42, 2960 (1977).
Merck Index, 9th ed., p. ONR-60.
J. Chem. Soc. Chem. Comm. No. 13, pp. 713–714 (1982).
Jeffrey & McCombie, J. Org. Chem. 43, 587 (1982).
A. Yoshida, T. Hayoshi, N. Takeda, S. Ohda & E. Olki Chem. Pharm. Bull. 29, 2899 (1981).

Primary Examiner—Nicholas S. Rizzo

Attorney, Agent, or Firm—Raymond M. Speer; Hesna J. Pfeiffer; Gabriel Lopez

[57] ABSTRACT

Disclosed are 6- and 6,6-disubstituted-2-substituted thiopen-2-em-3-carboxylic acids of the following structure:

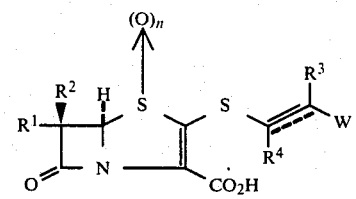

wherein: $R^1$, $R^2$, $R^3$, and $R^4$ are independently selected from: hydrogen; substituted and unsubstituted: alkyl, cycloalkyl, halo, alkoxyl, alkenyl, aralkyl, aryl, heterocyclyl, heteroaryl, and heterocyclylalkyl; W is an electron withdrawing group, and, for example, is selected from: $-COR^5$, $-CN$, $SO_2C_6H_5$; $R^5$ is hydrogen; substituted and unsubstituted: alkyl, aryl, aralkyl, heteroaryl, heterocyclyl, or heterocyclylalkyl; or $R^5$ may be $-OR^6$, $-NR^7R^8$, and $-SR^9$; wherein $R^6$ is H; substituted and unsubstituted: alkyl, alkenyl, or a group which defines $-CO_2R^6$ as a pharmaceutically acceptable ester wherein $R^6$ is, for example, phthalidyl, or 5-methyl-2-oxo-1,3-dioxolen-4-ylmethyl; $R^7$ and $R^8$ are independently selected from: hydrogen; substituted and unsubstituted: alkyl, aralkyl, aryl, heterocyclyl, and heterocyclylalkyl; $R^9$ is substituted and unsubstituted: alkyl, aralkyl, aryl, heterocyclyl, and heterocyclalkyl; $R^3$ may also be W; n is 0 or 1; when the unsaturated moiety attached to the exocyclic sulfur atom is acetylenic, then $R^3$ and $R^4$ are nonexistent and W is as previously defined. Such compounds I are new and they and their pharmaceutically acceptable salt and ester derivatives are useful as antibiotics.

5 Claims, No Drawings

2-UNSATURATED ALKYLTHIO-PEN-2-EM-3-CARBOXYLIC ACIDS

BACKGROUND OF THE INVENTION

This invention relates to 2-unsaturatedalkythio-pen-2-em-3-carboxylic acids and their pharmaceutically acceptable salts and esters which are useful as antibiotics I:

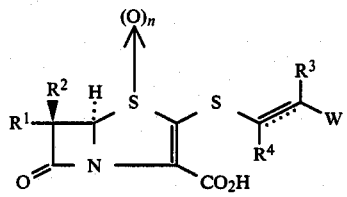

wherein $R^l$, $R^2$, $R^3$ and $R^4$ are independently selected from: hydrogen; substituted and unsubstituted; alkyl, alkoxyl and alkenyl having from 1-6 carbon atoms; cycloalkyl having 3-6 carbon atoms; halo (chloro, fluoro, bromo); aralkyl having from 7-14 carbon atoms, such as benzyl; aryl, such as phenyl; heteroaryl, heterocyclyl and heterocyclylalkyl, wherein the heterocyclic ring comprises 4-6 members, one or more being selected from oxygen, nitrogen and sulfur and the alkyl moeity has from 1-6 carbon atoms; wherein the substituent or substituents on $R^l$, $R^2$, $R^3$ and $R^4$ are selected from halo (chloro, bromo, fluoro, iodo), hydroxyl, alkoxyl, cyano, carboxyl, carbamoyl, amino, and the above recited values for $R^1$, $R^2$, $R^3$ and $R^4$; n is 0 or 1; W is an electron withdrawing group, which may be selected from $—COR^5$, CN, and $SO_2C_6H_5$; wherein $R^5$ is hydrogen; substituted and unsubstituted: alkyl having 1-6 carbon atoms; aryl and aralkyl having 6-14 carbon atoms, such as phenyl and benzyl; cycloalkyl having 3-6 carbon atoms; heteroaryl, heterocyclyl and heterocyclylalkyl, wherein the heterocyclic ring comprises 4-6 members, one or more being selected from oxygen, nitrogen, and sulfur and the alkyl moiety has from 1-6 carbon atoms; or $R^5$ may be: $—OR^6$, $—NR^7R^8$, or $—SR^9$; wherein $R^6$ is hydrogen; or substitued and unsubstituted: alkyl or alkenyl having 1-6 carbon atoms, or a group which defines $—CO_2R^6$ as a pharmaceutically acceptable ester, wherein $R^6$ is, for example, phthalidyl, or 5-methyl-2-oxo-1,3-dioxolen-4-ylmethyl; $R^7$ and $R^8$ are independently selcected from: hydrogen, and substituted and unsubstituted: alkyl having 1-6 carbon atoms; aryl, aralkyl having 7-14 carbon atoms, such as benzyl; and heteroaryl, heterocyclyl, and heterocyclylalkyl (as defined above): $R^9$ is selected from the same group comprising $R^7$ and $R^8$, but excludes hydrogen; wherein: the substitutent or substituents on the above-defined radical groups are selected from: halo (chloro, bromo, fluoro, iodo), hydroxyl, alkoxyl, cyano, carboxyl, carbamoyl, amino, and the above recited values for $R^l$, $R^2$, $R^3$ and $R^4$; $R^3$ may also be W; when the unsaturated moiety attached to the exocyclic sulfur atom is acetylenic, then $R^3$ and $R^4$ are nonexistent and W is a previously defined.

This invention also relates to a process for preparing the penem antibiotic of structure I, above. This process involves the reaction of an appropriately substituted 2-thiopenam 1:

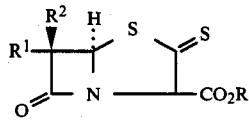

with a Michael reagent in the presence of base; wherein $R^l$ and $R^2$ are as previously defined and R is a removable protecting group.

This invention also relates to a process for preparing 6- and 6,6-disubstituted-2-substituted thio-pen-2-em-3-carboxylic acids Ia:

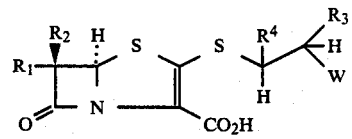

wherein $R^1$, $R^2$, $R^3$, $R^4$, and W are as previously defined, and their pharmaceutically acceptable salts and esters which are useful as antibiotics.

The common intermediate for the preparation of novel compounds I and compounds Ia, the 2 thioxopenam 1, above, is described in co-pending concurrently filed U.S. patent application Ser. No. 460,729 of F. P. DiNinno, W. J. Leanza and R. W. Ratcliffe filed concurrently with the present application. The cited application is fully incorporated herein by reference to the extent that it teaches the preparation of intermediates; and penem antibiotics; which utility is common to the final antibiotic compound of the present invention.

There is a continuing need for new antibiotics. For, unfortunately, there is no static effectiveness of any given antibiotic; because continued wide scale usage selectively gives rise to resistant strains of pathogens. In addition, the known antibiotics suffer from the disadvantage of being effective only against certain types of microorganisms. Accordingly, the search for new antibiotics continues.

Thus, it it an object of the present invention to provide a novel class of antibiotics which are useful in animal and human therapy and in inanimate systems. These antibiotics are active against a broad range of pathogens which representively include both Gram-positive bacteria such as *S. aureus, Strep. pyogenes,* and *B. subtilis,* and Gram-negative bacteria such as *E. coli,* Pseudomnas, *Proteus morganii,* Serratia, and Klebsiella. Further objects of this invention are to provide chemical processes for the preparation of such antibiotics and their nontoxic pharmaceutically acceptable salts and esters; pharmaceutical compositions comprising such antibiotics; and to provide methods of treatment comprising administering such antibiotics and compositions when an antibiotic effect is indicated.

DETAILED DESCRIPTION OF THE INVENTION

The following diagram conveniently summarizes the process of the present invention;

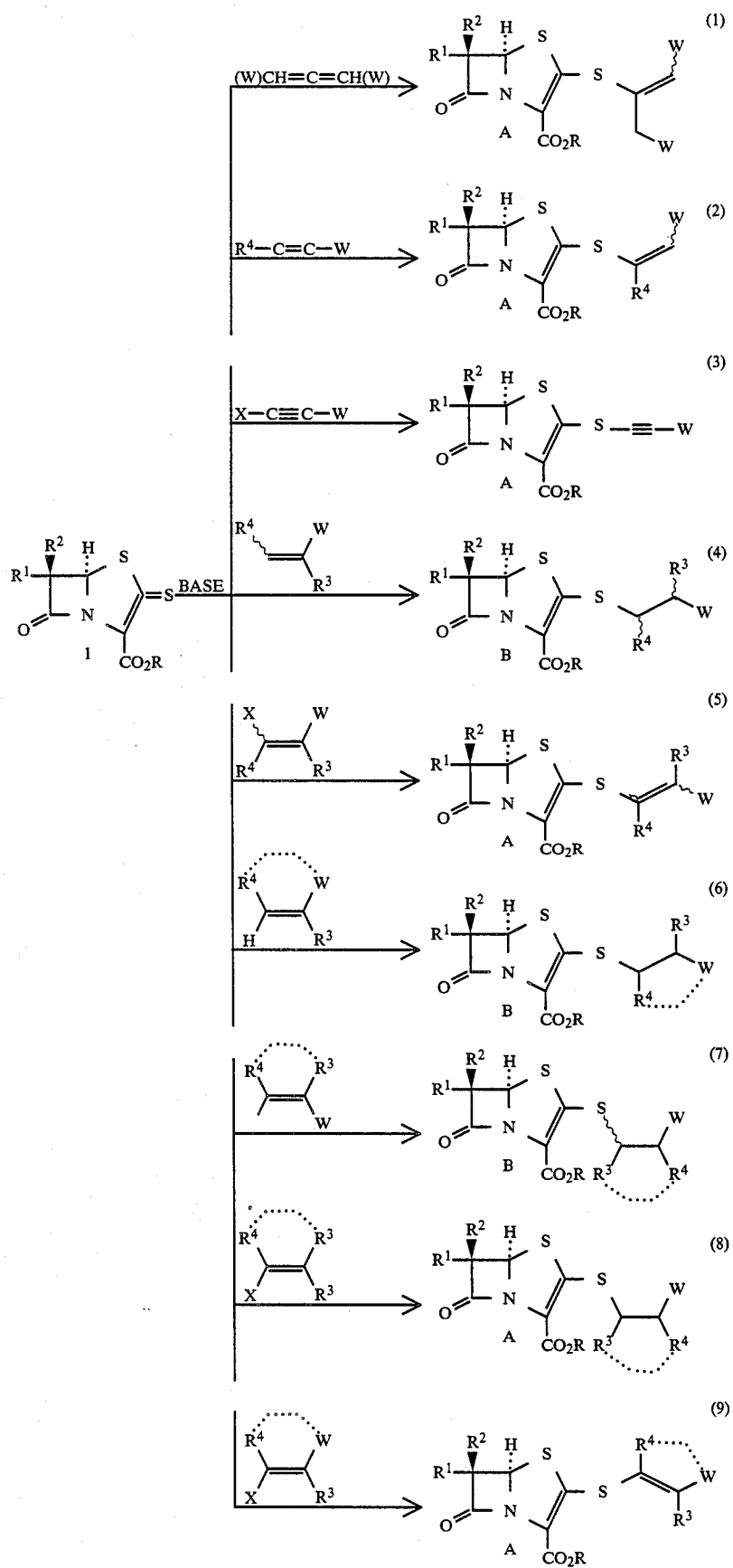

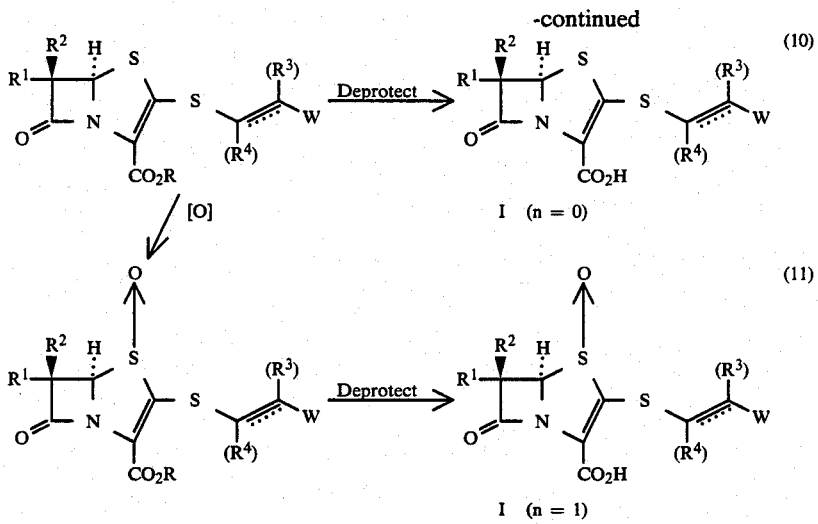

In words relative to the foregoing equations, the 2-thioxopenams 1 are readily prepared in either racemic or enantiomerically pure state according to the above-cited, and incorporated-by-reference, concurrently filed application of DiNinno, Leanza, and Ratcliffe; see also U.K. patent application GB No. 2074563A; or *J. Chem. Soc. Chem. Comm.* No 13, pp. 713–714 (1982), which are incorporated herein by reference. Base mediated reactions of thioxopenams 1 with electron deficient olefins, allenes, and acetylenes result in the formation of new penems A and known penems B, above. Such reactions of a nucleophile and an electron deficient acceptor are commonly referred to as Michael type reactions. (See Merck Index, 9th ed., page ONR-60.) By the Michael type reactions of thioxopenams 1, as depicted above, is meant those that fall into two general reaction classes: (a) addition to the electron deficient substrate (commonly known as Michael acceptors); and (b) addition-eliminations, in which the Michael acceptor is suitably disposed to accomodate the expulsion of the leaving group X. X is typically bromo, iodo, sulfonyloxy, phosphoryloxy, or the like. Bases such as diisopropylethylamine, triethylamine, diazabicycloundecene (DBU), diazabicyclooctane (DABCO), sodium hydride, lithium hexamethyldisilazide, or the like, may be employed in the reaction with 1 in a solvent such as acetonitrile, N,N-dimethylformamide, tetrahydrofuran, methanol, toluene, or the like, at a temperature of from −78° C. to 80° C. for from a few minutes to 72 hours. The electron deficient olefins, allenes, and acetylenes are known, commonly employed synthetic reagents and are explicitly defined below for the purpose of representative disclosure; but this listing does not limit the scope of the invention. In addition, the nature of the Michael acceptor maybe cyclical in two general arrays, in which the electron withdrawing component can either be endocyclic or exocyclic. The reactions of thioxopenam (1) as given in equations 4, 6, and 7 provide diastereomeric mixtures of products whereas the analogous reactions of equations 1, 2 and 5 usually provide geometric mixtures of olefins. In equation 2, when W=CN, only the Z-olefin geometry predominates, the result of the formal trans addition of the thioxopenam to the acetylene.

$R^1$, $R^2$, $R^3$, $R^4$, and W are as previously defined. R is an ester protecting group selected from allyl, p-nitrobenzyl, o-nitrobenzyl, acetonyl, or the like. The preferred groups are $R^1$=(R)Me CH(OR') where R'=tert-buytl dimethylsilyl and hydrogen, $R_2$=H, R=allyl, $R^3$ and $R^4$=H, $CH_3$ and W=CN, $CONH_2$.

Oxidation of the penem esters A and B is conveniently performed using established procedures; see for example the following U.S. patent applications assigned to Merck & Co., which are incorporated herein by reference to the extent that they define the oxidated transformation:

1. U.S. Ser. No. 353,452, filed March 1, 1982; now abandoned
2. U.S. Ser. No. 353,451, filed March 1, 1982; now abandoned
3. U.S. Ser. No. 353,450, filed March 1, 1982; now U.S. Pat. No. 4,388,320
4. U.S. Ser. No. 353,454, filed March 1, 1982, now abandoned and
5. U.S. Ser. No. 353,453, filed March 1, 1982, now abandoned in which A or B is treated with 1.0–1.5 equivalents of an oxidant such as m-chloroperoxybenzoic acid, peracetic acid, hydrogen peroxide, sodium hypochlorite, or the like, in an inert solvent such as dichloromethane, tetrahydrofuran, dioxane, or the like at a temperature of from −78° C. to 23° C. for from a few minutes to several hours.

The deprotection of penems A and B to their biologically active forms I and Ia, respectively, is accomplished by established procedures.

When $R^1$ or $R^2$ is a protected hydroxyalkyl group the hydroxy protecting group may be removed prior to or simultaneously with the removal of the ester blocking group. Typically when the protecting group is tert-butyldimethylsilyl it is removed prior to deesterification by treatment with 3 eq. of tetrabutylammonium fluoride buffered with 10 eq. of glacial acetic acid in tetrahydrofuran solution at 23° for 24–72 hours. When the hydroxy protecting group is p-nitrobenzyloxycarbonyl and the ester group is p-nitrobenzyl they are removed simultaneously by hydrogenation (below).

The final deblocking step to I and Ia is accomplished by conventional procedures such as hydolysis or hydrogenation. Typically A and B when R is p-nitrobenzyl in a solvent such as dioxane-waterethanol, tetrahydrofuran-aqueous dipotassium hydrogen phosphate-isopropanol, or the like, is treated under a hydrogen pressure of from 1 to 4 atmosphere in the presence of a hydrogenation catalyst such as palladium on charcoal, palladium hydroxide, or the like at a temperature of from 0 to 50° C. for from 0.5 to 4 hours to provide I or Ia.

When R is allyl, the ester is removed by the method of Jeffrey and McCombie, J. Org. Chem. 43, 587 (1982). Typically the penem allyl ester is stirred in a solvent such as methylene chloride, ethylacetate or tetrahydrofuran with potassium or sodium 2-ethylhexanoate and a catalytic amount of tetrakistriphenylphosphine palladium O at ambient temperature for from 15 minutes to 1 hour. The potassium salt of the penem usually precipitates from solution or may be precipitated by the addition of Et$_2$O and is recovered by filtration.

PREPARATION OF STARTING MATERIALS

The following diagram conveniently summarizes the preparation of 1

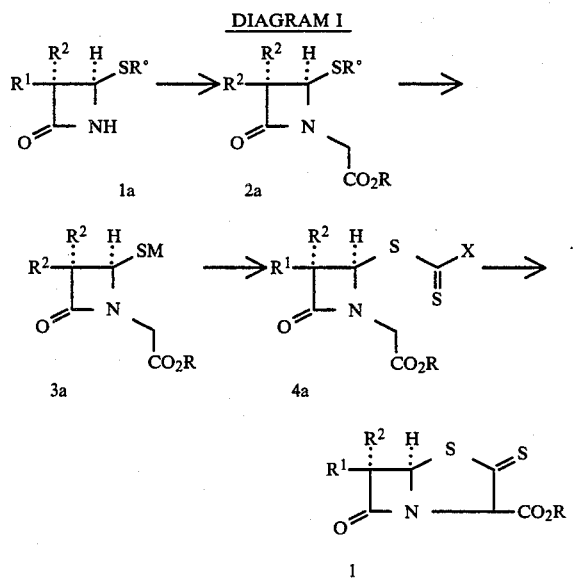

DIAGRAM I

In words relative to the above diagram, the azetidinone starting material 1a is known, or can readily be prepared by known methods. Representative, and representatively preferred values for $R^1$ and $R^2$ are given below. $R^0$ in starting material 1a must be a group which allows the formation of a carbonium ion. Preferred values for $R^0$ include, trityl, bis (p-methoxyphenyl)-methyl, 2,4-dimethoxybenzyl, and the like. The most preferred value for $R^0$ is trityl. As defined above, the most preferred values for R include allyl, p-nitrobenzyl, and the like. The conversion 1a to 2a is accomplished by treating 1a in a solvent such as benzene, toluene, xylene, DMF, or the like, in the presence of powdered fused potassium hydroxide, sodium hydride, potassium t-butoxide, Triton B or the like, and 18-crown-6 or a tetraalkylammonium salt, or the like with a bromoacetic ester such as allylbromoacetate, p-nitrobenzylbromo acetate, or the like, for from 0.5 to 4 hours at a temperature of from 0° to 80° C.

The conversion 2a to 3a is accomplished by treating 2a in a solvent such as methanol, ethanol, butanol, or solvent mixtures such as methanolmethylene chloride, or the like, in the presence of pyridine, picoline, lutidine, 4-dimethylaminopyridone, or the like, with a thiophilic metal salt reagent wherein the metal is silver, mercury, thallium or the like and the salt portion is nitrate, triflate, acetate, or the like, for from 0.1 to 3 hours at a temperature of from 0° to 60° C. The most preferred thiophilic metal is silver, and the most preferred silver reagent is silver nitrate.

The conversion 3a to 4a is accomplished by treating 3a in a solvent such as methylene chloride, benzene, tetrahydrofuran, or the like, with a halothiocarbonate ester of the formula:

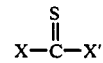

wherein: X'=chloro, bromo, and X is an aryloxy, arylthio, alkylthio, alkoxy or halo group, for example, in the presence of pyridine, picoline, lutidine, 4-dimethylaminopyridine, or the like, at a temperature of 0° to 30° C. for from 0.5 to 2 hours. [In the foregoing, alkyl is 1-6 carbon atoms; and aryl is phenyl.]

In general, the cyclization 4a to 1 is accomplished in the presence of base. For example, cyclization 4a to 1 may be accomplished by treating 4a in a solvent such as tetrahydrofuran, toluene, ether, dioxane, or the like, or mixtures thereof in the presence of lithium hexamethyldisilazide, lithium 2,2,6,6-tetramethyl piperidide, lithium triethyl methoxide, sodium hydride, potassium t-butoxide, or the like, in the presence of hexamethylphosphoramide, 1,3-dimethyl-2-imidazolidinone (DMI) or the like, at a temperature of from −78° to 23° C. for from 0.1 to 8 hours. Alternatively, the conversion of 4 to 5 is accomplished by treating 4a in a solvent such as, methylene chloride, chloroform, tetrahydrofuran, benzene, or the like, in the presence of 1,8-diazabicyclo[5.4.0]undec -7-ene, diisopropylethylamine, 1,5-diazabicyclo[4.3.0]non-5-ene; 1,8-bis(dimethylamino)-naphtalene, or the like, at a temperature of from 20° to 80° C. for from 1 to 18 hours. Starting materials 1a are known, or are prepared according to known methods. The most preferred situation finds $R^1$=H and $R^2$ is as defined above, such as, alkyl having 1-6 carbon atoms and hydroxylsubstituted alkyl, for example, CH$_3$CH(OH); wherein the hydroxyl function is typically protected by a triorganosilyl group, such as, t-butyldimethylsilyl (TBDMS), or the like. The racemic tritylthioazetidionone 1 may be prepared according to U.K. patent No. 2,042,514 (1980), which is incorporated herein by reference; the preferred chiral azetidinone 1 ($R^1$=H, $R^2$=protected hydroxyethyl) can be prepared from 6-APA by the method of A. Yoshida, T. Hayoshi, N. Takeda, S. Ohda and E. Olki Chem. Pharm. Bull. 29, 2899 (1981), citing the procedure of F. Di Ninno, U.S. Pat. No. 4,168,314 (1979) and J. Org. Chem. 42, 2960 (1977) who used a p-nitrobenzyl (PNB) blocking group on the OH instead of TBDMS. These publications are all incorporated herein by reference. Other, representative values of $R^1$ and $R^2$ are listed below.

| DEFINITION OF $R^1$ and $R^2$ | |
|---|---|
| —H | $\underset{\underset{}{-\text{CHCH}_2\text{F}}}{\overset{\text{OH}}{\|}}$ |
| —CH$_3$ | |
| —CH$_2$CH$_3$ | $\underset{\underset{\text{H}}{\|}}{\overset{\overset{\text{OH}}{\|}}{-\text{C}-\text{CF}_3}}$ |
| —CH$_2$CH$_2$OH | |

| -continued |
|---|
| DEFINITION OF $R^1$ and $R^2$ |
| —CH₂OH |
| —CH(CH₃)₂ |
| —OCH₃ |
| $\quad$ OH<br>$\quad$ \|<br>—CHCH₂Cl |
| —CH₂CH₂Cl |
| —CHCH₃<br>$\quad$ \|<br>$\quad$ F |
| $\quad$ OH<br>$\quad$ \|<br>—C—CH₃<br>$\quad$ \|<br>$\quad$ CH₃ |
| $\quad$ OH<br>$\quad$ \|<br>—C—◁ |
| $\quad$ OH<br>$\quad$ \|<br>—CHCH₂CH₃ |

The most preferred 2-thioxopenams bear at ring position number 6 the 1-hydroxyethyl substituent. The most preferred configuration of these thioxopenams is 8R, 6S, 5R.

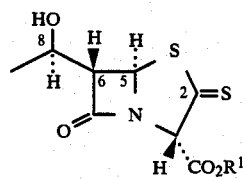

With regard to the preparation of the preferred 2-thioxopenams of the present invention, the following diagram specifically recites their synthesis.

DIAGRAM II

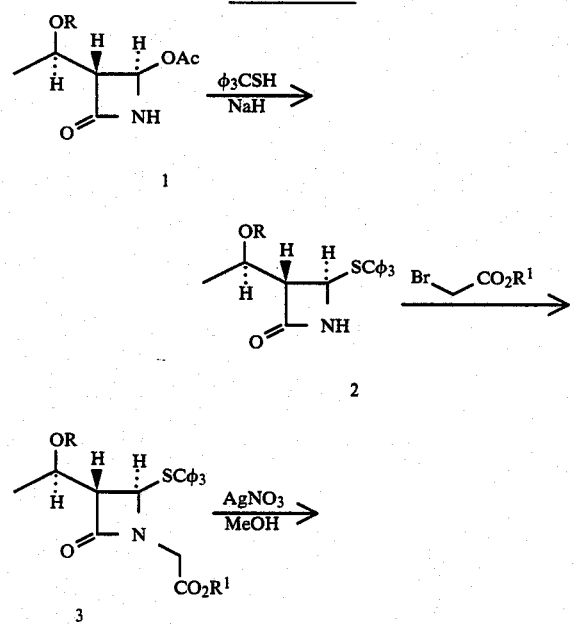

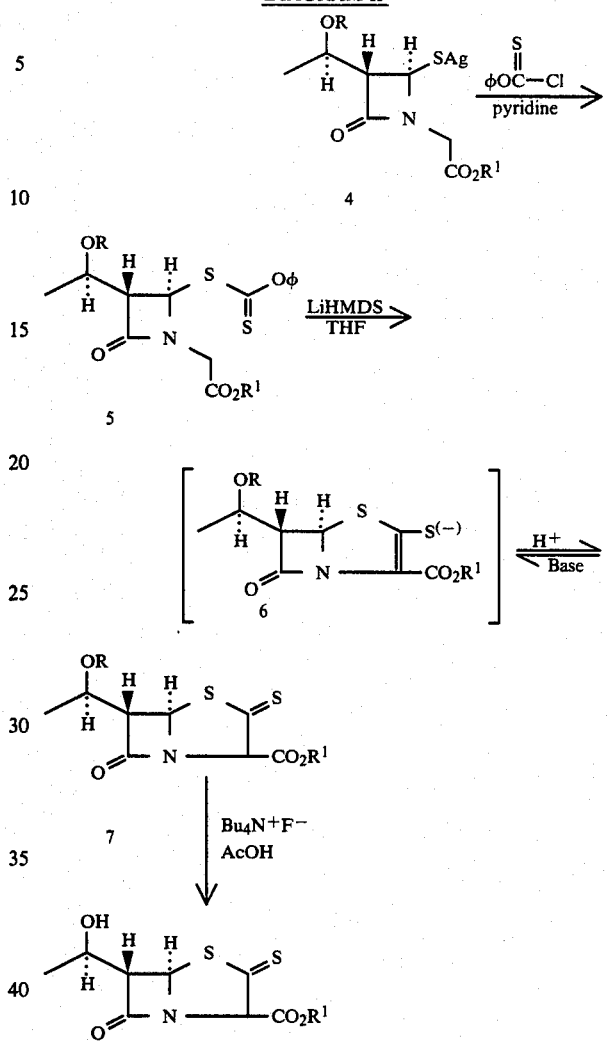

R = t-butyldimethylsilyl
φ = phenyl
$R^1$ = CH₂CH=CH₂ or p-nitrobenzyl (PNB)

Step I

In the preferred process (3R,4R)-4-acetoxy-3-[(R)-1-(tert-butyldimethylsilyloxy)ethyl]-2-azetidinone (1) is stirred with sodium triphenylmethylmercaptide in DMF solvent at 0° C. for 45 minutes to produce after workup and isolation (3S,4R)-4-triphenylmethylthio-3-[(R)-1-(tert-butyldimethylsilyloxy)ethyl]-2-azetidinone (2). Alternatively intermediate (2) can be produced by exposure of 1 to tritylmercaptan in methanolic sodium methoxide.

Step II

The tritylthioazetidinone 2 is treated with 1.5 equivalents of allyl bromoacetate and powdered potassium hydroxide in benzene solvent at ambient temperature in the presence of dicyclohexyl-18-crown-6 for 4 hours. The resulting (3S,4R)-1-(allyloxycarbonyl)methyl-3-[(R)-1-(tert-butyldimethylsiloxy)ethyl]-4-triphenylmethylthio-2-azetidinone (3) is isolated by conventional means. Alternatively p-nitro-benzylbromoacetate may be substituted for allylbromoacetate.

Step III

The azetidinone 3 is treated with a methanolic solution of silver nitrate in the presence of pyridine in methanol solvent at 0° C. for 0.5 hours. After removal of the water-soluble salts the crude mixture containing the silver thiolate 4 is preferably carried into the next step but may be purified by conventional techniques, such as preparative thin layer chromatography. The solvent methanol employed herein serves a dual purpose in that it reacts with the incipient trityl carbonium ion to form trityl methyl ether, which need not be separated from the silver thiolate, as it is inert to the reagents used in Step IV and may be conveniently separated later. The process of forming silver thiolates from 4-tritylthioazetidinone and their acylation has been described in the U.K. Pat. No. 2,042,520A, which is incorporated above. This invention adopts that process to specifically form a 4-dithiocarbonate ester of an azetidinon-1-yl acetic ester giving the critical intermediate 4 for the hitherto unknown cyclization reaction in Step V.

Step IV

The crude silver thiolate obtained from Step III is thioacylated with phenoxythiocarbonyl chloride in methylene chloride solvent in the presence of pyridine at 0° C. for 20 minutes. The chlorothiocarbonate ester employed herein is not critical, however, the leaving group X should not be so reactive that is undergoes elimination under the conditions of the thioacylation reaction, leading to side reactions; nor so weakly reactive that it is displaced with difficulty during Step V. Phenoxy and substituted phenoxy are preferred for group X, although alkoxy, alkylthio and arylthio may be used. From 0.1 to 1.0 equivalents of pyridine or a similar organic base is used to catalyze the reaction. In the preferred case it is not necessary to purify the resulting phenoxythiocarbonyl derivative 5 for use in the next step, particularly if purified silver thiolate is used in the reaction.

Step V

Purified (3S,4R)-1-(allyloxycarbonyl)methyl-3-[(R)-1-(tert-butyldimethylsilyloxy)ethyl]-4-phenoxy(thiocarbonyl)thio-2-azetidinone (5) is treated with 2.75 equivalents of the preferred base lithium hexamethyldisilazide at −78° C. in anhydrous tetrahydrofuran containing some 1,3-dimethyl-2-imidazolidinone (DMI), which appears to make the reaction proceed more uniformly, under an atmosphere of nitrogen. After 5–15 minutes, the mixture is neutralized with dilute hydrochloric acid, although other organic acids such as acetic, trifluoroacetic, and p-toluenesulfonic acids, as well as aqueous buffers, may be used, and worked up to give the desired 2-thioxopenams 7. Alternatively, a strong organic base such as diazabicycloundecene (DBU) will give slow cyclization of 5 to 7 at room temperature.

Although in the preferred process the hydroxy group is protected by a t-butyldimethylsilyl group, the presence of this group is not necessary during all of the steps in the reaction sequence. It may be conveniently removed from the thioxo penam (7) or it may be removed earlier in the sequence (e.g., from 3) and be replaced with a more readily hydrolyzable group such as trimethylsilyl just before the cyclization to (6).

DEFINITIONS OF $R_3$, $R_4$, W, AND MICHAEL ACCEPTORS FOR THE FORMATION OF PENEMS OF TYPE A.

| $R^3$ | $R^4$ | W | Michael Acceptor Reagent | |
|---|---|---|---|---|
| | | | | A |
| H | H | $CONH_2$ | $H-C\equiv CCONH_2$ | |
| H | H | $CO_2Me$ | $H-C\equiv C-CO_2Me$ | |
| H | H | CN | $H-C\equiv C-CN$ | |
| H | $CH_3$ | CN | $CH_3-C\equiv C-CN$ | |
| H | H | CN | $BrCH=CHCN$ | |
| H | H | $CONH_2$ | $BrCH=CHCONH_2$ | |
| H | H | $CONMe_2$ | $H-C\equiv C-CONME_2$ | |
| H | $-CH_2CO_2Me$ | $CO_2Me$ | $MeO_2CCH=C=CHCO_2Me$ | |
| H | $-CH_2CN$ | CN | $HCCH=C=CHCN$ | |
| H | $-CH_2CONH_2$ | $CONH_2$ | $H_2NCOCH=C=CHCONH_2$ | |
| $CH_3$ | H | CN | $BrCH=C\begin{smallmatrix}CN\\CH_3\end{smallmatrix}$ | |
| H | H | COMe | $H-C\equiv C-COMe$ | |
| H | H | $SO_2\phi$ | $H-C\equiv C-SO_2\phi$ | |
| H | $-\overset{O}{\underset{\|}{C}}-$ | $-\overset{O}{\underset{\|}{C}}NH-$ | (pyrrolinedione with Br) | |

-continued

DEFINITIONS OF $R_3$, $R_4$, W, AND MICHAEL ACCEPTORS FOR THE FORMATION OF PENEMS OF TYPE A.

| $R^3$ | $R^4$ | W | Michael Acceptor Reagent |
|---|---|---|---|
| $-CH_2-$ | $-CH_2-$ | CN | (cyclobutene with CN and Br) |
| H | $-CH_2CH_2$ | $-\overset{O}{\underset{}{C}}-$ | (cyclopentenone with Br) |
| $-CH_2-$ | $-CH_2$ | $-CONH_2$ | (cyclobutene with $CONH_2$ and Br) |

A: (β-lactam structure with $R^1$, $R^2$, H, S, $S-C\equiv C-W$, $CO_2R$)

| | |
|---|---|
| $CO_2Me$ | $Br-C\equiv C-CO_2Me$ |
| $CONH_2$ | $Br-C\equiv C-CONH_2$ |
| CN | $Br-C\equiv C-CN$ |

DEFINITION OF MICHAEL REAGENTS FOR THE PRODUCTION OF KNOWN PENEMS OF TYPE B.

B: (β-lactam structure with $R^1$, $R^2$, H, S, SR', $CO_2R$)

| Michael Acceptor Reagent | 2-Substituted Thio Side Chain Formed, SR' |
|---|---|
| $CH_2=CHCOCH_3$ | $-SCH_2CH_2COCH_3$ |
| $CH_2=CHCN$ | $-SCH_2CH_2CN$ |
| $CH_3CH=CHCOCH_3$ | $-SCH(CH_3)CH_2COCH_3$ |
| (maleimide, NH) | (thio-succinimide, NH) |
| (3-methyl maleimide, NH) | (3-methyl thio-succinimide, NH) |
| $CH_2=C(CH_3)COCH_3$ | $-SCH_2C(CH_3)COCH_3$ |
| (maleic anhydride) | (thio-succinic anhydride) |
| (N-methyl maleimide) | (N-methyl thio-succinimide) |
| (N-benzyl maleimide, $NCH_2\phi$) | (N-benzyl thio-succinimide, $NCH_2\phi$) |
| (cyclopentene-1,3-dione) | (thio-cyclopentane-1,3-dione) |
| (pyrrolinone, NH) | (thio-pyrrolidinone, NH) |

-continued
DEFINITION OF MICHAEL REAGENTS FOR THE PRODUCTION OF KNOWN PENEMS OF TYPE B.

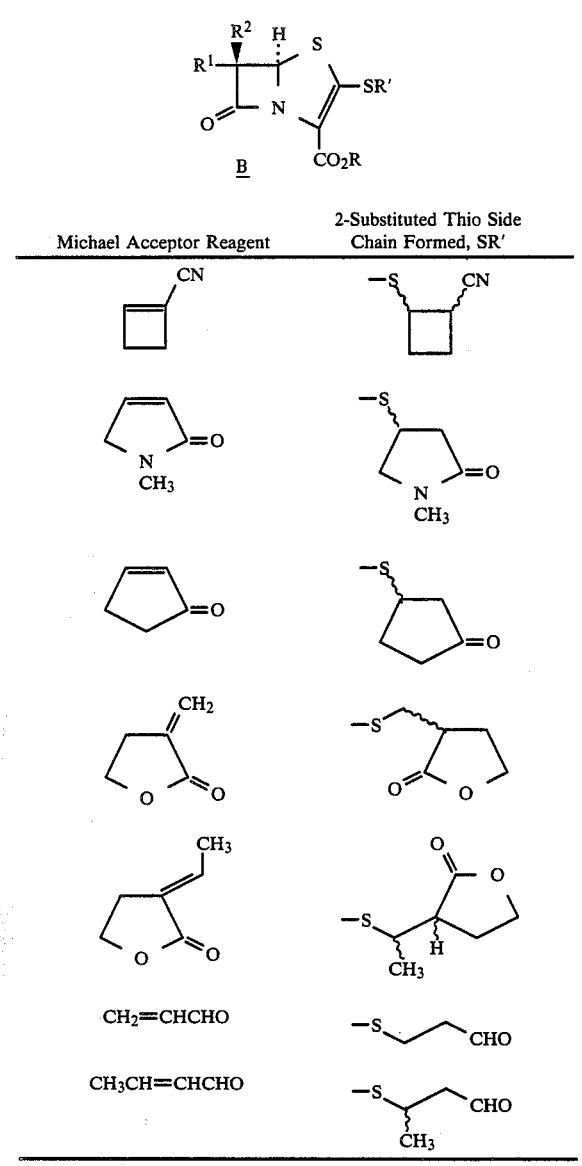

φ = phenyl

The most preferred penems of the present invention bear at ring position number 6 the 1-hydroxyethyl substituent and posses the 8R, 6S, 5R absolute cofigurations. Such preferred penems of the can be prepared according to the following diamgrams, which specifically recite their synthesis.

DIAGRAM III

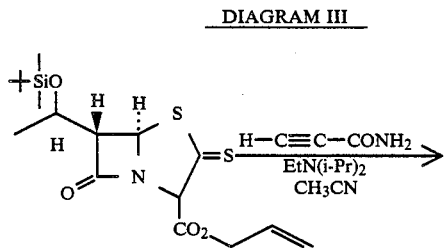

-continued
DIAGRAM III

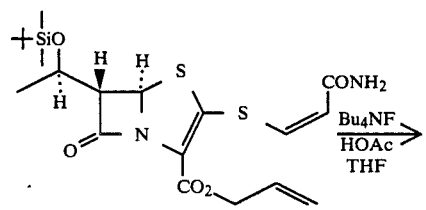

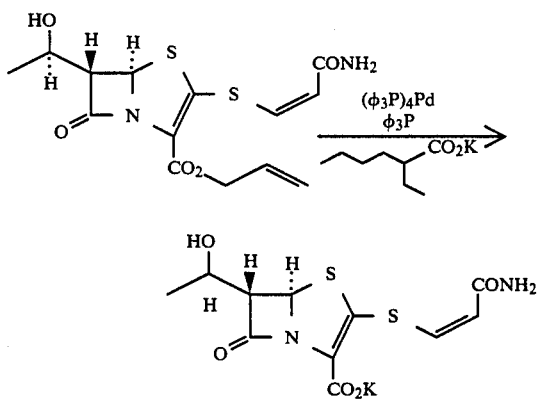

DIAGRAM IV

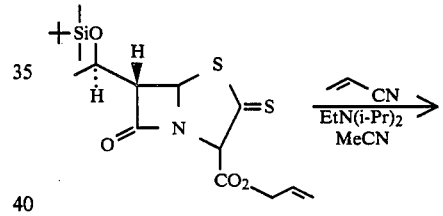

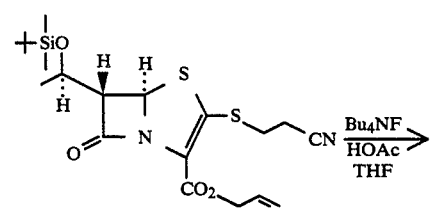

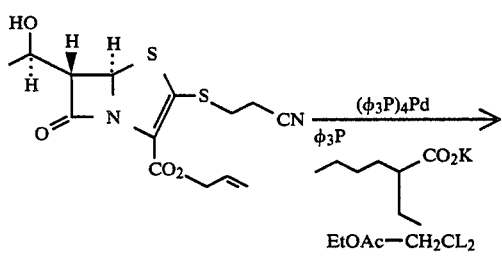

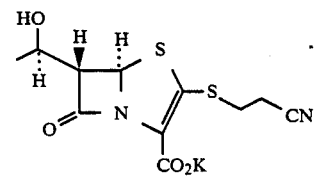

DIAGRAM V

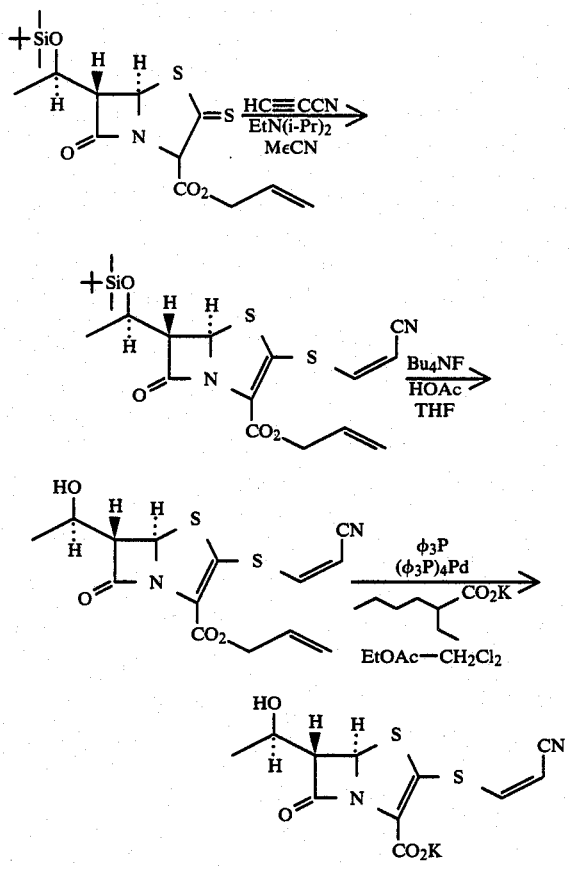

Relative to Structures I and Ia, above, the most preferred values for the 3-carboxylic acid esters and amides may be represented in the following way:

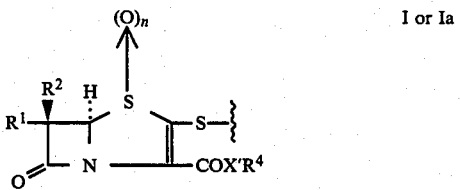

wherein X' is oxygen, sulfur or NR' (R' is hydrogen or loweralkyl having from 1 to 6 carbon atoms); and $R^4$ is hydrogen, or, inter alia, is representatively selected to provide the pharmaceutically acceptable salt, ester, anhydride ($R^4$ is acyl), and amide moieties known in the bicyclic β-lactam antibiotic art; $R^4$ may also be a readily removable blocking group, or a synthetically useful salt. A synthetically useful salt moiety consists of a highly lipophilic carboxylate cation which imparts organic solubility to the molecule. This type of carboxylate derivative allows reactions, and particularly the displacement reaction of I to II, to be conducted in an organic solvent. Representative examples of such highly lipophilic carboxylate cations $R^4$ are ammonium salts $R_4{}^aN^+$ wherein $R^a$ are independently selected from 1-16 carbon alkyl groups or 7-10 carbon aralkyl groups. A particularly useful example of this type is N,N-dimethyl-N-benzyl-N-hexadecyl ammonium salt.

Identification of the Radical —COX'$R^4$

In the generic representation of the compounds of the present invention (I, above), the radical represented by —COX'$R^4$ is, inter alia, —COOH (X' is oxygen and $R^4$ is hydrogen) and all radicals known to be effective as pharmaceutically acceptable ester, anhydride ($R^4$ is acyl) and amide radicals in the bicyclic β-lactam antibiotic art, such as the cephalosporins and penicillins and nuclear analogues thereof.

Suitable blocking esters $R^4$ (X=0) representatively include:

(i) $R^4 = CR^aR^bR^c$ wherein at least one of $R^a$, $R^b$, and $R^c$ is an electrondonor, e.g., p-methoxyphenyl. The remaining $R^a$, $R^b$ and $R^c$ groups may be hydrogen or organic substituting groups. Suitable ester groups of this type include p-methoxybenzyloxycarbonyl.

(ii) $R^4 = CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, 2,2,2-trichloroethoxycarbonyl, and acetonyloxycarbonyl.

(iii) $R^4 = CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl, triphenylmethoxycarbonyl, and allyloxycarbonyl.

Silyl esters. This category of blocking groups $R^4$, may conveniently be prepared from a halosilane of the formula: $R_3{}^{4'}SiX'$; wherein X' is a halogen such as chloro or bromo and $R^{4'}$ is independently chosen from: alkyl having 1-6 carbon atoms, phenyl, or phenylalky. Suitable esters of this type include t-butyldiphenylsilyloxycarbonyl.

Pharmaceutically acceptable carboxyl derivatives of the present invention are those derived by reacting I with alcohols, acylating reagents and the like. For example, esters and amides of interest are the above-listed starting materials and final products having the —COX'$R^4$ group at the 3-position; wherein X' is oxygen, sulfur or NR' (R' is H or $R^4$), and $R^4$ is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl-and nitro- substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representatives of such amides are those wherein R' is selected from the group consisting of hydrogen and alkyl such as methyl and ethyl.

The most preferred —COX'R⁴ radicals of the present invention are those wherein (relative to Structure I above), X' is oxygen and R⁴ is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa, Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of prinicipal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semisolid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

In the foregoing word description of the invention, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents.

The following examples demonstrate the preparation of representative members of the genus defined by Structure I. It is to be understood that the purpose of this recitation is to further illustrate the invention and not to impose any additional limitation. All temperatures are in ° C.

EXAMPLES—SECTION A

Example 1

Allyl-trans-2-(3-(1-t-butyldimethylsilyloxyethyl)-4-silverthio-2-azetidinon-1-yl)acetate

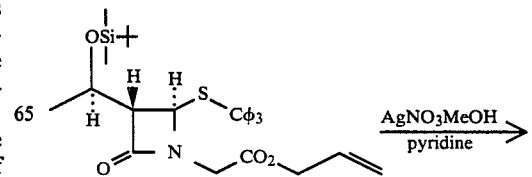

-continued

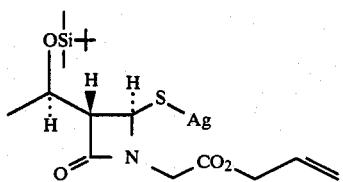

To a solution of allyl tran-2-(3(1-t-butyldimethyl-silyloxyethyl)-4-triphenylmethylthio-2-azetidinon-1-yl)acetate (126 mg, 0.223 mmol) in 1 ml of methanol at 0° was added pyridine (27 μl) followed by a solution of silver nitrate in methanol (2.32 ml of 0.12M solution). After stirring for 30 minutes, the methanol was rapidly evaporated under vacuum and the residue was taken up in 7 ml of methylene cloride. The solution was washed three times with 8 ml portions of water, dried over anhydrous magnesium sulfate and evaporated. The residue was chromatographed on a thin layer silica gel plate eluted with toluene-ethyl acetate (7:3). The band between 4.5 and 11 cm was extracted with methanol to afford the desired product. Yield 76 mg, (73%) of a white solid. NMR δ(200 MHz, CDCl$_3$), 3.10 (dd, J=4.2 and 1.8, H3), 5.21 (d, J=1.8, H4).

Example 2

Allyl-trans-2-(3-(1-t-butyldimethylsilyloxyethyl)-4-phenoxythiocarbonylthio-2-azetidinon-1-yl)acetate

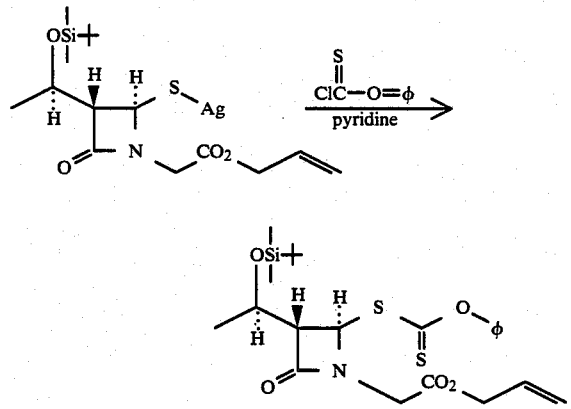

To a cooled (0°) solution of allyl trans 2-(3-(1-t butyl-dimethylsilyloxyethyl)-4-silverthio-2-azetidinon-1-yl)acetate (104 mg, 0.223 mmol) in 4 ml of methylene chloride was added phenoxythiocarbonyl chloride (30 μl, 0.223 mmol) followed by pyridine (18 μl). After 20 minutes the solution was evaporated to dryness under reduced pressure. The residue was taken up in methylene chloride and the precipitated silver chloride was removed by filtration. The filtrate was concentrated and chromatographed on a silica gel plate developed with 9:1 toluene-ethyl acetate. The band at 5.5–8.5 cm was isolated with ethyl acetate. Yield 69 mg, (62%) of product as an oil. NMRδ(200 MHz, CDCl$_3$), 3.34 (dd, J=6 and 2.5, H3), 5.88 (d and m, J=2.5, H4 and vinylic methylene).

Example 3

Allyl-trans-6-(1-t-butyldimethylsilyloxyethyl)-2-thioxopenam-3-carboxylate

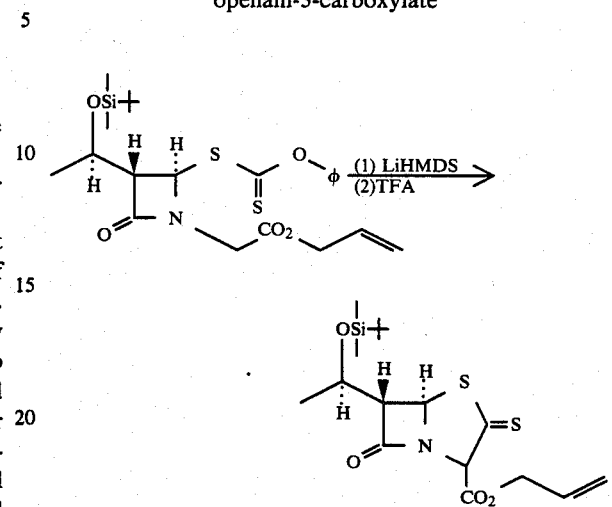

Procedure A:

A solution of butyllithium (217 μl of 2.3M solution in hexane) was added to a solution of hexanethyldisilizane (106 μl) in tetrahydrofuran (0.68 ml) at room temperature. After 30 minutes, the solution was cooled to −78° and added to a cooled (−78°) solution of allyl trans 2-[3-(1-t-butyldimethylsilyloxyethyl)-4-phenoxythiocarbonylthio-2-azetidinon-1-yl)acetate (100 mg, 0.17 mmol) in 1ml tetrahydrofuran. The solution was stirred for 20 minutes then neutralized with trifluoroacetic acid (15 μl). The solution was diluted with methylene chloride (8 ml) and washed successively with 0.1 M, pH 7 phosphate buffer (6 ml) and water (2×6 ml), then dried (MgSO$_4$) and evoporated. The product was purified by thin layer chomatography eluted with methylene chloride-toluene (6:1). Yield 68 mg, (84%). NMRδ(200 MHz, CDCl$_3$), 3.65 (d, J=1.5, H6), 5.35 (s, H3 and m, vinylic methylene), 5.9 (s, H5 and m, vinylic methine).

Procedure B:

A solution of allyl trans 2-[3(1-t-butyldimethylsilyloxyethyl)-4-phenoxythiocarbonyl]thio-2-azetidinon-1-yl)acetate (12.2 mg, 0.025 mmol) and 1,8-diazabibyclo[5.4.0] undec-7-ene (7.4 μl) in 0.4 ml of THF was stirred at 23° for 8 hours. To the resulting solution of thioxopenam was added methyliodide (20 μl) and the solution was stirred for one hour. The solution was worked up as in procedure A to give 4.8 mg of the above described methylthiopenem.

Example 4

P-nitrobenzyl-trans-2-[3-(1-t-butyldimethylsilyloyethyl)-4-triphenylmethylthio-2-azetidinon-1-yl) acetate

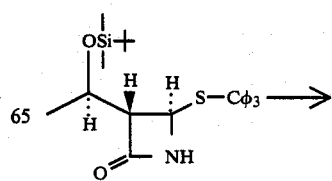

-continued

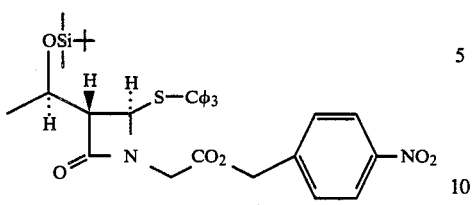

Powdered, fused potassium hydroxide (125 mg, 2.25 mmol) and 18-crown-6 (20 mg) were added to a solution of 3-(1-t-butyldimethylsilyloxyethyl)-4-triphenylmethylthio-2-azetidinone (775 mg, 1.5 mmol) in 7 ml of benzene. The mixture was stirred at room temperature while a solution of P-nitrobenzyl bromoacetate (620 mg, 2.25 mmol) in benzene (7 ml) was added dropwise during one hour. After an additional hour of stirring, 0.5M, pH 7 phosphate buffer (20 ml) was added and the benzene layer was separated, dried (MgSO4) and evaporated. The residual oil was chromatographed on silica gel (2×25 cm column) eluted with methylene chloride. There was first obtained a fraction containing starting azetidinone (230 mg) followed by the desired product (710 mg, 68% yield). NMR$\delta$(200 MHz, CDCl$_3$), 3.42 (t, J=2.3, H3), 4.56 (d, J=2.3, H4).

Example 5

P-nitrobenzyl-trans-2-[3-(1-t-butyldimethylsilyloxyethyl)-4-silverthio-2-azetidinon-1-yl) acetate

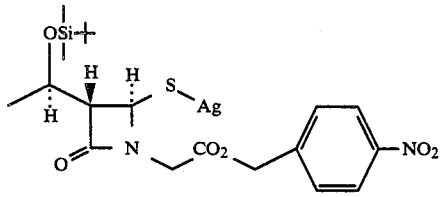

To a cooled (0°) solution of p-nitrobenzyl trans 2-[3-1-t-butyldimethylsilyloxyethyl)-4-triphenylmethylthio-2-azetidinon-1-yl)acetate (55 mg, 0.079 mmol) in 1 ml of methanol was added pyridine (10 μl) and 0.12 M silver nitrate in methanol (0.82 ml). A precipitate immediately formed. The mixture was stirred at 0° for 30 minutes then the precipitate was recovered by filtration, washed with methanol and dried under nitrogen giving a white powder (44 mg). This was dissolved in methylene chloride and the solution was washed three times with water, dried (MgSO4) and evaporated leaving the desired product as a yellow resin. NMR$\delta$(200 MHz, CDCl$_3$), 3.10 (dd, J=4.2 and 1.8, H3), 5.12 (d, J=1.8, H4).

Example 6

P-nitrobenzyl-trans-2-(3-(1-t-butyldimethylsilyloxyethyl)-4-phenoxythiocarbonylthio-2-azetidinon-1-yl) acetate

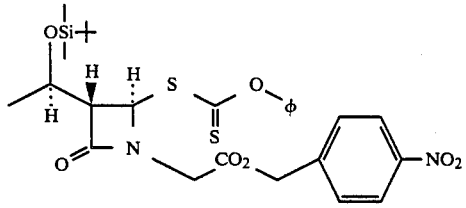

P-nitrobenzyl trans 2-[3-(1-t-butyldimethylsilyloxyethyl)-4-silverthio-2-azetidinon-1-yl)acetate (177 mg, 0.32 mmol) was dissolved in 2 ml of methylene chloride and the solution was cooled to 0°. Phenoxythiocarbonylchloride (43 μl, 0.32 mmol) and pyridine (26 μl) were added and the mixture was stirred for 20 minutes. The mixture was centrifuged and the supernatant liquid was concentrated and chromatographed on silica gel plates developed with toluene-ethyl acetate (9:1) The band at Rf 0.4 was isolated giving the desired product as a strawcolored oil. Yield, 85 mg, (46%). NMR$\delta$(200 MHz, CDCl$_3$), 3.34 (dd, J=6 and 2.8, H3), 5.84 (d, J=2.8, H4).

Example 7

P-nitrobenzyl-trans-6-(1-t-butyldimethylsilyloxyethyl)-2-thioxo-penam-3-carboxylate

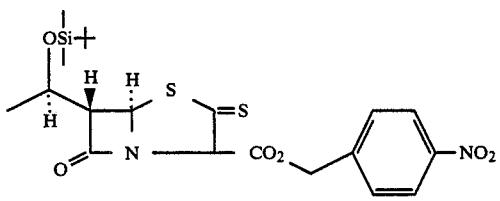

P-nitrobenzyl trans 2-(3-(1-t-butyldimethylsilyloxyethyl)-4-phenoxythiocarbonylthio-2-azetidinon-1-yl)acetate (74 mg, 0.125 mmol) was dissolved in 1 ml of dry tetrahydrofuran and the solution was cooled to −78°. Lithium hexamethyldisilazide (0.6 ml of 0.5 M solution) was added and the solution was stirred for 20 minutes. The solution was diluted with methylene chloride (5 ml) then neutralized with glacial acetic acid (29 μl). The solution was extracted with pH 7 phosphate buffer and with water, then dried over MgSO4 and evaporated. The residue was purified by thin layer chromatography (2% methanol in chloroform) giving 33 mg (53%) of the desired product. NMR$\delta$(200 MHz, CDCl$_3$), 3.68 (dd, J=4 and 1, H6), 5.42 (s, H3), 5.89 (d, J=1, H5).

Example 8

Chiral Synthesis (+)-(3S,4R)-3-(1-R-t-butyldimethylsilyloxy)-4-triphenylmethylthio-2-azetidinone

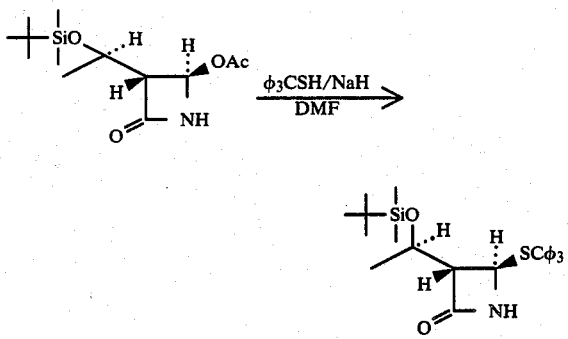

To a stirred suspension of 1.3 g (0.033 moles) of 61% NaH dispersion in 25 ml of sieve dried DMF at 0° C. under an atmosphere of nitrogen was added dropwise a solution of 9.12 g (0.033 moles) of trityl mercaptan in 50 ml of sieve dried DMF over a period of 23 minutes. The resulting mixture was stirred further at 0° C. under nitrogen for 10 minutes, after which time a solution of (3S,4R)-4-acetoxy-3-(1-R-t-butyldimethylsilyloxy)azetidinone (8.62 g, 0.03 moles) in 50 ml of sieve dried DMF was added over a period of 20 minutes. The mixture was stirred further at 0° C. under nitrogen for 0.5 hours and was then poured onto a mixture of ice-$H_2O$ and saturated, aqueous $NH_4Cl$ solution and extracted wth $Et_2O$. The $Et_2O$ extract was washed twice with $H_2O$ and then with saturated NaCl solution, dried over anhydrous $Na_2SO_4$, filtered, and evaporated. Purification by column chromatography on 500 g EM-60 silica gel eluting with $CH_2Cl_2$ gives 12.9 g, (85%) of product; $[\alpha]_D+3.7$ (c 8, $CHCl_3$); mp. 94°–96.5° C.

Example 9

Allyl-(3S,4R)-2-(1-R-t-butyldimethylsilyloxyethyl)-4-triphenylmethylthio-2-azetidinon-1-yl)acetate

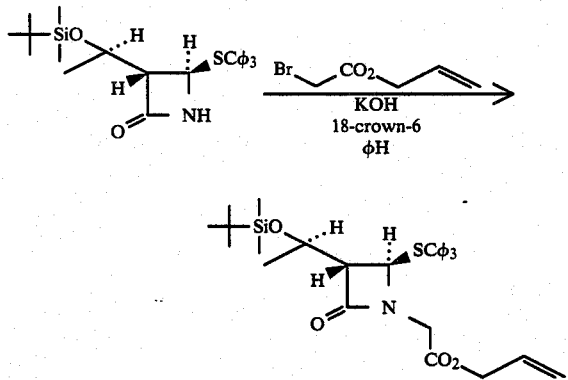

According to the procedure of T. Kamazaki, et al., *Heterocycles*, 15, 1101 (1981), 5.04 g (0.01 moles) of (+)-(3S,4R)-3-(1-R-t-butyldimethylsilyloxy)- 4-triphenylmethylthio-2-azetidinone, 926 mg (0.0165 moles) of powdered KOH, and a catalytic amount of 18-crown-6 was stirred in 50 ml of benzene at ambient temperature and was treated with a solution of 2.67 g (0.015 moles) of allylbromoacetate in 30 ml benzene (added dropwise over 30 minutes) at ambient temperature for 5 hours. After this time the mixture was partitioned between EtOAc and ice-$H_2O$. The organic phase was separated, washed with saturated NaCl solution, dried over anhydrous $Na_2SO_4$, filtered and evaporated. Purification by column chromatography on 300 g of EM-60 silica gel eluting with $CH_2Cl_2$ and 2% EtOAc in $CH_2Cl_2$ gives 3.74 g (62%) of the product as a colorless oil; $[\alpha]_D+0.8$ (c 20, $CHCl_3$)

Example 10

Allyl-(3S,4R)-2-(3-(1-R-t-butyldimethylsilyloxyethyl)-4-phenoxythiocarbonylthio-2-azetidinon-1

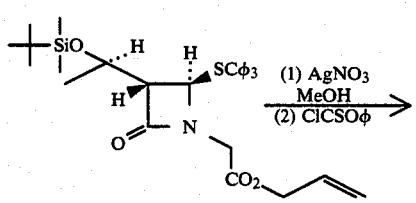

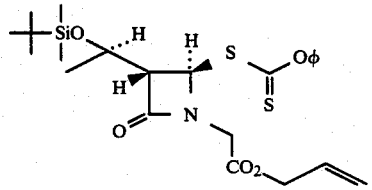

To a stirred solution of 3.74 g (6.2 mmoles) of allyl (3S,4R)-2-(3-(1-R-t-butyldimethylsilyloxyethyl)-4-triphenylmethylthio-2-azetidinon-1-yl)acetate in 30 ml MeOH at 0° C. was added sequentially 738.4 mg (9.3 mmoles) of neat pyridine and then 45.6 ml of 0.15M $AgNO_3$ solution in MeOH. The resulting mixture was stirred at 0° C. under nitrogen for 0.5 hours after which time the mixture was concentrated in vacuo and partitioned between $CH_2Cl_2$ and ice-$H_2O$. The organic phase was separated, dried over anhdyrous $Na_2SO_4$, filtered, evaporated, and dried in vacuo. The residue so obtained was dissolved in 30 ml $CH_2Cl_2$, stirred, cooled to 0° C., and treated sequentially with 500 μl of pyridine and 1.18 g (6.85 mmoles) of phenoxythio chloroformate. After stirring at 0° C. under an atmosphere of nitrogen for 20 minutes, the insolubles were removed by filtration through celite and washed well with EtOAc. The filtrate was partitioned between EtOAc, ice-$H_2O$, and 2N HCl. The organic phase was separated, washed with saturated NaCl solution, dried over anhydrous $Na_2SO_4$, filtered, and evaporated. Purification of the residue by chromatography on 100 g of EM-60 silica gel eluting with $CH_2Cl_2$-$\phi Me$ (10:1) provides 2.23 g (72%) of the desired product, as a yellow oil; $[\alpha]_D+59.6$ (c 13.6, $CHCl_3$).

Example 11

Allyl-(5R,6S)-6-(1-R-t-butyldimethylsilyloxyethyl)-2-thioxopenam-3-carboxylate

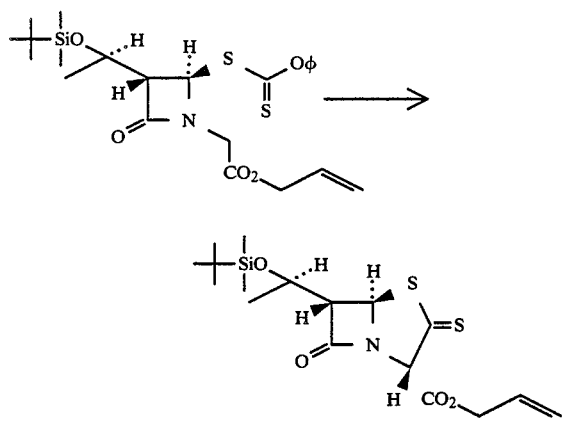

To a stirred solution of freshly prepared lithium hexamethyldisilazide (0.54 mmoles) in 5 ml anhydrous THF containig 100 µl of 1,3-dimethyl-2-imidazolidinone at −78° C. under a nitrogen atmosphere was added a solution of 96.6 mg (0.195 mmoles) of allyl (3S,4R)-2-(3-(1-R-t-butyldimethylsilyloxyethyl)4-phenoxythiocarbonylthio-2-azetidinon-1-yl)acetate in 800 µl of anhydrous THF. The resulting mixture was stirred at −78° C. under nitrogen for 4 minutes and then was partitioned between EtOAc, ice-H$_2$O aand 2N HCl. The organic phase was separated, washed with saturated NaCl solution, dried over anhydrous Na$_2$SO$_4$, filtered, and evaporated. The residue was purified by plate layer chromatography [one development CH$_2$CL$_2$] to give 53.2 mg (68%) of thioxopenam as an orange oil; [60 ]$_D$−31.70 (c 4.3, CHCl$_3$); λmax EtOH=316 nm; λmax Et$_3$N, EtOH=353.2 nm.

Example 12

Allyl-(5R,6S)-6-(1-R-hydroxyethyl)-2-thioxopenam-3-carboxylate

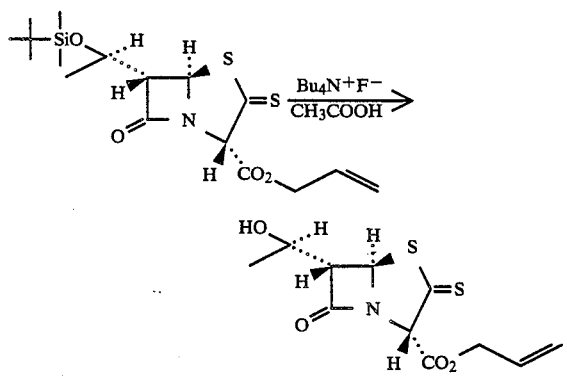

To a stirred solution of Allyl (5R, 6S)-6-(1-R-t-butyldimethylsilyloxyethyl)-2-thioxopenam-3-carboxylate (41.7 mg) 0.1 mmol) in 1ml of tetrahydrofuran at 0° was added glacial acetic acid (70 µl) followed by tetrabutylammonium fluoride (1M in TMF, 0.3 ml). The solution was stirred at room temperature for 24 hours then diluted with 5 ml of methylene chloride and extracted three times with 0.1M PH$_7$ phosphate buffer. The methylene chloride solution was dried (MgSO$_4$) and evaporated and the residue purified by plate-layer chromatography (5% MeOH in CHCl$_3$), providing 20 mg of the de-silyated thioxo penam allyl ester or a yellow oil. NMR (200 MHz, CDCl$_3$), δ3.65 (dd, J=1.5 and 6.5, H-6), 5.38 (S, H-3), 5.92 (d, J=1.5, H-5) [α]$_D$+22 (c 1.6, MeOH).

Example 13

P-nitrobenzyl- (5R, 6S)-6-(1-R-hydroxyethyl)-2-thioxopenam-3-carboxylate

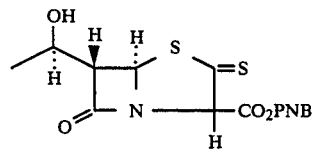

Following the procedure in Example 12 substituting p-nitrobenzyl (5R, 6S)-6-(1-R-t-butyldimethyl silyloxyethyl)-2-thioxopenam-3-carboxylate for the corresponding allyl ester, there is obtained the de-silyated thioxopenam p-nitrobenzyl ester.

EXAMPLES—SECTION B

Example 1

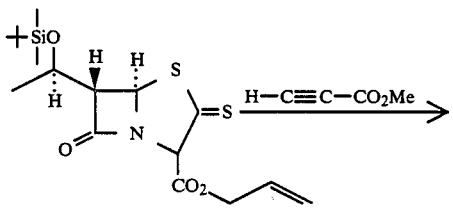

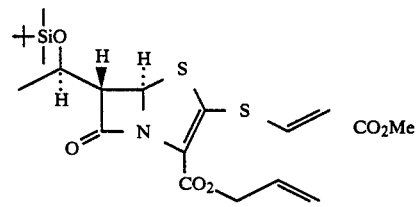

Allyl-(5R, 6S)-6-[(R)-1-t-butyldimethylsilyloxyethyl-[2-(2-carbomethoxyvinylthio)]-penem-3-carboxylates To a stirred solution of 81.1 mg (0.2 mmol) of chiral thioxopenam in 2 ml of sieve dried acetonitrile at ambient temperature was added sequentially 18 µL (0.1 mmol) of neat diisopropylethylamine and 20 µl (0.22 mmol) of neat methylpropiolate. The mixture was stirred at ambient temperature under an atomosphere of nitrogen for 40 minutes. After this time the mixture was partitioned between EtOAc/ice-H$_2$O/2N HCl(aq.)and the organic phase separated, washed with an aqueous, saturated NaCl solution, dried over anhydrous Na$_2$SO$_4$, filtered, and evaporated. Purification of the residue by plate layer chromatography [2 developments CH$_2$Cl$_2$] gave 21.1 mg (21.5%) of the E-isomer of the title penem; IR (CH$_2$Cl$_2$)1800, 1715(br)cm$^{-1}$; NMR (CDCl₃) δ0.08 (s,6H), 0.88 (s,9H), 1.24 (d, J=6Hz,3H), 3.76 (bs,4H), 4.26 (m,1H), 4.72 (m,2H), 5.26 and 5.42 (m,2H), 5.68 (app.bs, 1H), 5.94 (m,1 H), 6.16 (d, J=15.5Hz,1 H), 7.82(d,J=15.5Hz, 1H); UV(dioxane) λ$_{max}$342 nm, 271 nm; and 71.5 mg (72.9%) of the Z-isomer of the title penem; IR (CH₂Cl₂) 1799 and 1705 cm⁻¹; NMR (CDCl₃)δ0.08 (s,6H), 0.87 (s,9H), 1.27 (d, J=6.5 Hz), 3.77 (dd, J=1.5, 4.5 Hz, 1H ), 3.79 (s,3H), 4.27 (m, 1H ), 4.75 (m,2H), 5.27 and 5.44 (m,2H), 5.64 (d,J=1.5Hz,1H), 5.94 (m,1H), 6.03 (d, J=10Hz, 1H), and 7.39 (d, J=10Hz,1H); UV (dioxane)λ$_{max}$342 nm, 272 nm.

Example 2

Allyl-(5R-6S)-6-[(R)-1-t-butylidimethylsilyloxyethyl]-2-(2-cyanovinylthio)-pen-2-em-3-carboxylate

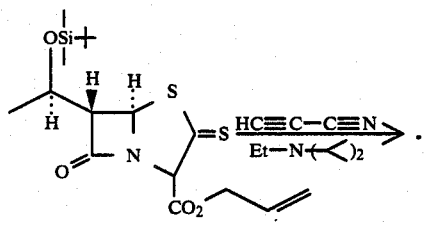

To a stirred solution of allyl (5R,6S) -[1-R-t-butyldimethylsilyloxyethyl]-2-thioxopenem-3-carboxylate (94.3 mg, 0.24 mmol) in 8 ml of sieve dried acetonitrile at 0° C. was added 20.5 μl (0.12 mmol) of diisopropylethylamine and 19.1 μl (0.3 mmol) of cyanoacetylene. The mixture was stirred at 0° C. for 15 minutes and then partitioned between ethyl acetate and cold dilute aqueous HCl. The organic phase was separated, washed with brine, dried over anhydrous magnesium sulfate and evaporated. Purification by plate layer chromotography (2% ethylacetate in methylene chloride) afforded 89.9 mg (84%) of the titled penem; I.R. (CH₂Cl₂) 2220, 1792, 1710 (sh), 1692. NMR .08 (S, 6H) .88 (S, 9H), 1.26 (d, J=6HZ, 3H), 3.79 (dd, J=1.5, 4.5 HZ, 1H), 4.28 (m, 1H), 4.76 (m, 2M), 5.29 (m, 1H), 5.44 (m, 1H), 5.56 (d, J=10 HZ, 1H) 5.71 (d, J=1.5 Hz, 1H) 5.94 (m, 1H) and 7.42 (d, J=10 Hz, 1H);λmax342 nm, 325nm (sh), 269nm; [α]$_D$+333(cl,CHCl₃); mp 122°-123° C.

Example 3

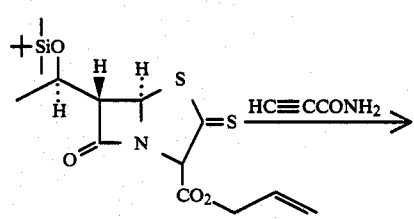

-continued

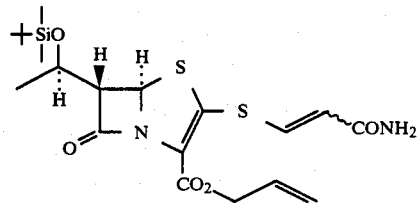

Allyl-(5R, 6S)-6-[(R)-1-t-butyldimethylsilyloxyethyl]-2-(2-carbamoylvinylthio)-penem-3-carboxylates.

To a stirred solution of 182.8mg (0.456 mmol) of chiral thioxopenam in 15 mL of sieve dried acetonitrile at 0° C. was added sequentially 40 μl (0.228 mmol) of diisopropylethylamine and a solution of 37.7 mg (0.547 mmol) of propiolamide in 0.5 mL acetonitrile. The reaction mixture was stirred at 0° C. for 1.5 hr and then at ambient temperature for 20 hr under an atmosphere of nitrogen. After this time, the reaction mixture was partitioned between EtOAc/ice-H₂O/2.5N HCl and the organic phase separated, washed with staurated NaCl solution, dried over Na₂So₄, filtered, and evaporated. Punification by plate layer chromatography on silica gel GF [one development EtOAc-CH₂Cl₂ (1:1)]gave 159.4mg (74%) of a 3:1 mixture of Z and E isomers respectively of the title penems. Through a combination of recrystallization (boiling CH₂Cl₂-pet ether) and plate layer chromatography the isomers were obtained pure; Z-isomer: IR(CH₂Cl₂ 3500, 3390, 1780, 1690 (sh), 1670 cm⁻¹; NMR (CDCl₃)δ0.08 (s,6H), 0.88 (s,9H), 1.26 (d,J=6,5Hz,3H), 3.74 (dd, 1.5 and 4.5 Hz, 1H), 4.26 1H), 4.74 (m,2H), 5.26, 5.44,5.9 (3m,3H), 5.62 (d, J=1.5Hz, 1H), 5.8 (br s, 2H), 6.04 (d,J=9.5 Hz, 1H), 7.26 (d, J=9.5Hz, 1H); UV (dioxane)λ 267, 342 nm ; [α]$_D$+222 (c 1,CHCl₃); E$^{max}$-Isomer: IR (CH₂Cl₂) 3500, 3400, 1790, 1680 (br) cm⁻¹; NMR (CDCl₃)δ0.06 (s,6H), 0.86 (s,9H), 1.25 (d, J=6.5 Hz,3H), 3.74 (dd, J=1.5 and 4 Hz, 1H), 4.26 (m, 1H), 4.72 (m,2H), 5.26, 5.4, and 5.92 (3m, 3H), 5.46 (br s, 2H), 5.68 (d, J=1.5 HZ, 1H), 6.91 (d, J=15Hz, 1H), and 7.79 (d, J=15Hz, 1H); UV (dioxane)λ$_{max}$ 267, 342 nm.

Example 4

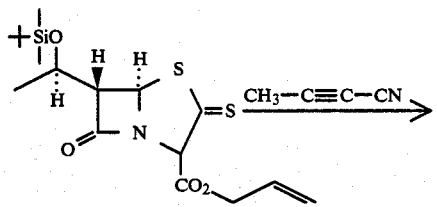

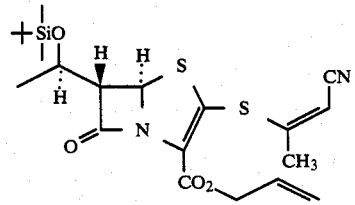

Allyl-(5R,6S)-6-[(R)-1-t-butyldimethylsilyloxy ethyl]-2-[Z-3-cyanoprop-2-enylthio]-penem-3-carboxylate To a stirred solution of 74.2 mg (o .185 mmol) of thioxopenam in 6 mL of sieve dried acetonitrile at 0° C. was added sequentially 16.1 μL (0.092 mmol) of diisopropylethylamine and 17.8 μL (0.24 mmol) of tetrolonitrile. The mixture was stirred at 0° C. for 5 minutes and at ambient temperature for 23 hour under an atmosphere of nitrogen. The mixture was partitioned between EtOAc/ice-H2O/2.5N HCl and the organic phase separated, washed with saturated NaCl solution dried over Na2SO4, filtered and evaporated. Purification by plate layer chromatography on silica gel GF [one development 1% EtoAc in CH2Cl2) gave 69 mg (80.4%) of the title penem which was recrystallized from boiling pet. ether-CH2Cl2; mp. 134°-142° C.; IR (CH2Cl2) 2225, 1790, and 1710 cm$^{-1}$; NMR (CDCl3)δ0.08 (s,6H), 0.88 (s,9H), 1.26 (d, J=6Hz, 3H), 2.32 (s,3H), 3.8 (dd, J=1.5 and 4.5 Hz, 1H), 4.28 (m, 1H), 4.75 (m,2H), 5.28 and 5.44 (2m,2H), 5.61 (s, 1H), 5.68 (d, J=1.5Hz, 1H), and 5.94(m, 1H); UV (dioxane)λ$_{max}$259, 325 (sh), 343 nm; MS m/e noM+ ; $^{m/e}$409 (M+-57); [α]$_D$+317 (c 2.27, CHCl3).

Example 5

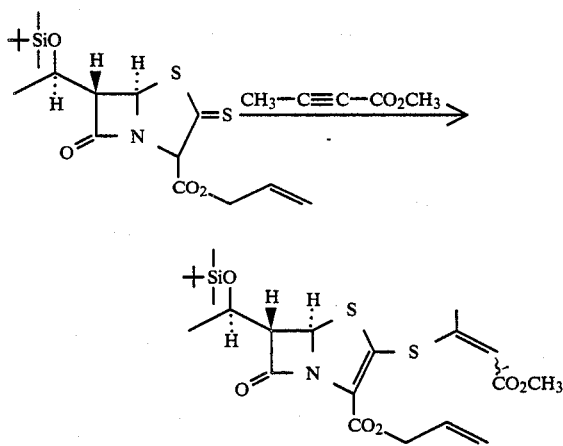

Allyl-(5R,6S)-6-[(R)-1-t-butyldimethylsilyloxy-ethyl]-2-[3-carbomethoxylprop-2-enylthio]penem-3-carboxylates.

A stirred mixture of 120 mg (0.299 mmol) of thioxopenam, 26.1 μL (0.15 mmol) of diisopropylethylamine, and 74 μL (0.75 mmol) of methyl tetrolate in 10 μL of sieve dried acetonitrile was heated at 65° C. under an atmosphere of nitrogen for 22.3 hr. The cooled mixture was partitioned between EtOAc/ice-H2O/2.5 N HCl and the organic phase, separated, washed with saturated NaCl solution, dried over Na2SO4, filtered, and evaporated. Purification by plate layer chromatography on silica gel GF [one development 2% EtoAc in CH2Cl2]gave 10.6 mg (7.1%) of the E-isomer of the title penem: IR (CH2Cl2) 1790, 1710 (br) cm$^{-1}$; NMR (CDCl3)δ0.08 (s,6H), 0.88 (s,9H), 1.24 (d, J=6 Hz, 3H), 2.54 (d, J=1Hz,3H), 3.74 (bs,4H), 4.28 (m,1H), 4.74 (m, 2H), 5.28 and 5.44 (2m, 2H), 5.66 (d,J=1.5Hz, 1H), 5.94 (m,1H), 6.2 (q, J=1Hz, 1H); and 25.4 mg (17%) of the Z-isomer of the title penem; IR (CH2Cl2) 1790, 1720 (br) cm$^{-1}$; NMR (CDCl3)δ0.06 (s,6H), 0.86 (s,9H), 1.22 (d, J=6Hz), 2.26 (d, J=1Hz, 3H), 3.76 (bs, 4H), 4.26 (m, 1H), 4.5 (m, 2H), 5.22 and 5.38 (2m, 2H), 5.62 (d, J=1.5Hz 1H), 5.9 (m,1H), 6.0 (q, J=1Hz,1H); MS m/e 499 (M+).

Example 6

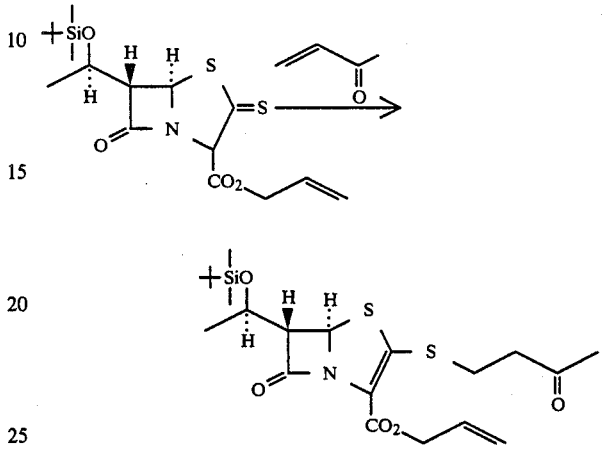

Allyl-(5R,6S)-6-[(R)-1-t-butyldimethylsilyloxyethyl]-2-[2-oxo-4-propylthio]-penem-3-carboxylate To a stirred solution of 20 mg (0.05 mmol) of thioxopenam in 0.5 mL of sieve dried acetonitrile at 0° C. was added sequentially 9.6 μL (0.055 mmol) of neat diisopropylethylamine and 4.5 μL (0.055 mmol) of neat methylvinylketone. The mixture was stirred at 0° C. under an atmosphere of nitrogen for 0.5 hr. The mixture was partitioned between EtOAc/ice-H2O/2.0 N HCl and the organic phase separated, washed with saturated NaCl solution, dried over Na2SO4, filtered and evaporated. Purification by plate layer chromotography [one development CH2CH2) gave 13.8 mg (59%) of the title penem; IR (CH2CH2) 1790, 1720, 1690 cm$^{-1}$; NMR (CDCl3)δ0.06 (s,6H), 0.88 (s,9H), 1.23 (d, J=2Hz, 3H), 2.18 (s,3H), 3.0 (m,2H), 5.3 and 5.5 (2m, 2H), 5.6 (d,J=1.5 Hz, 1H), and 5.86 (M, 1H); UV (dioxane)λ$_{max}$257, 337 nm.

Example 7

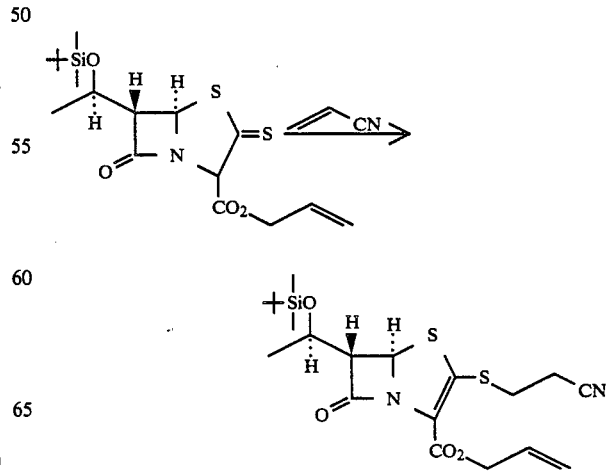

Allyl-(5R,6S)-6-[(R)-1-t-butyldimethylsilyloxyethyl]-2-[2-cyanoetylthio]-penem-3-carboxylate To a stirred solution of 22.6 mg (o .056 mmol) of thioxopenam in 0.5 mL of sieve dried acetonitrile at 0° C. was added sequentially 10.8 μl (0.062 mmol) of diisopropylethylamine and 15.6 μL (0.24 mmol) of acetonitrile. The reaction mixture was stirred at 0° C. for 0.5 hr and at room temperature for 24 hour under an atmosphere of nitrogen. The reaction mixture was worked up according to Example 6 and purified as previously described in U.S. patent application Ser. No. 460,729.

Example 8

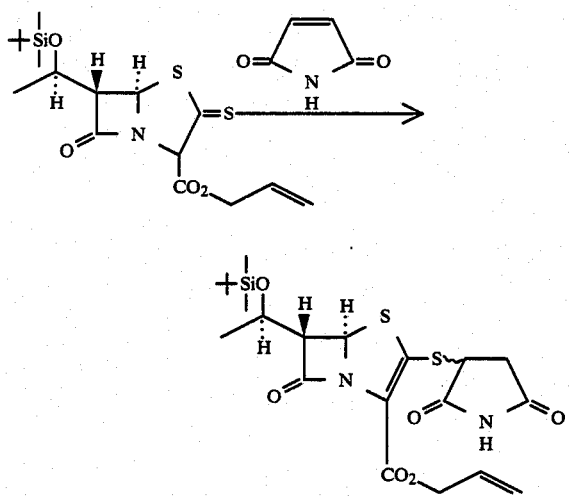

Allyl-(5R,6S)-6-[(R)-1-t-butyldimethylsilyloxyethyl]-2-[(R,S)-3-succinimidoylthio]-penem-3-carboxylate To a stirred solution of 60.1 mg (0.15 mmol) of thioxopenam in 1 mL of sieve dried acetonitrile at 0° C. was added sequentially 26.2 μL (0.15 mmol) of diisopropylethylamine and 16.0 mg (0.165 mmol) of maleimide. The reaction mixture was stirred at 0° C. for 20 minutes under an atmosphere of mitrogen. The reaction mixture was worked up in the manner as described in Example 6 and then purified by plate layer chromatography [one development $CH_2Cl_2$-EtOAc (9:1)]to give 39.5 mg (53%) of the title penem; IR ($CH_2Cl_2$) 3390, 1790, 1730, 1700 (sh) cm$^{-1}$; NMR($CDCl_3$)δ0.07 (s,6H), 0.87 (s,9H), 1.25 (d, J=6.5 HZ, 3H), 2.85 (m,2H), 5.26 and 5.41 (2m,2H), 5.68 and 5.76 (2d, J=1.5 HZ, 1H), 5.93 (m,1H), and 7.89 (brs, 1H); UV (dioxane)λ$_{max}$258, 339nm; MS m/e 498 (M+), 441, 344.

Example 9

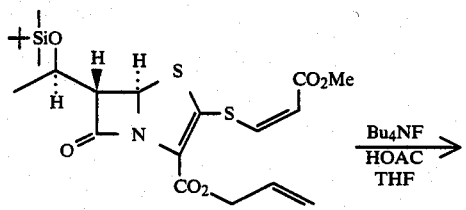

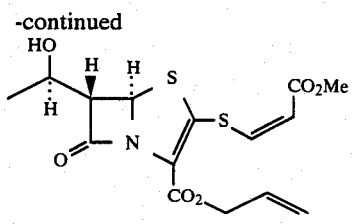

Allyl-(5R,6S)-6-[(R)-1-hydroxyethyl]-2-(Z-2-carbomethoxyvinylthio)-penem-3-carboxylate To a stirred solution of 32.2 mg (0.066 mmol) of the penem from Example 1 in 2 mL of tetrahydrofuran at ambient temperature under an atmosphere of nitrogen was added sequentially 38 μL (0.66 mmol) of neat glacial acetic acid and 199 μL (0.2 mmol) of a 1M solution of tetrabutylammonium fluoride in tetrahydrofuran. The reaction mixture was stirred at ambrient temperature under nitrogen for 18.5 hour. After this time, the reaction mixture was partitioned between EtOAc, ice-$H_2O$ and a saturated $NaHCO_3$ solution. The organic phase was separated, washed with an aqueous, saturated solution of NaCl, dried over $Na_2SO_4$, filtered, and evaporated. Purification of the residue by plate layer chromatoqraphy [one development $CH_2Cl_2$-EtOAc(5:1)]gave 15.0mg (61%) of the title penem; IR($CH_2Cl_2$) 3589, 1795, 1710 cm$^{-1}$; NMR ($CDCl_3$)δ1.39 (d,J=6.5 Hz, 3H), 1.77 (bd, J=5 Hz, 1H), 3.79 (s,3H), 3.81 (m,1H), 4.29 (m,1H), 4.76 (m,2H), 5.29 and 5.46 (2m, 2H}, 5.67 (bs, 1H), 5.98 (m,1H), 6.05 (d,J=10Hz,1H), and 7.37 (d,J=10 Hz,1H); UV (dioxane)λ$_{max}$272, 342 nm.

Example 10

Allyl-(5R,6S)-6-[(R)-1-hydroxvethvl]-2-(E-2-carbomethoxyvinylthio)-penem-3-carboxylate

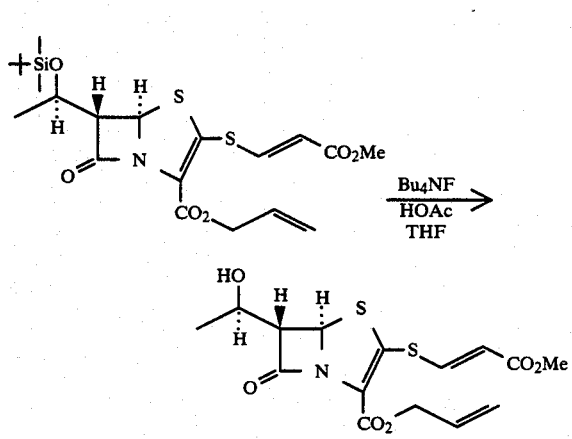

Following the procedure of Example 9, 21.1 mg (0.044 mmol)of penem from Example 1, 24.9 μL (0.44 mmol) of glacial acetic acid, and 130.5μL (0.13 mmol) of a 1M tetrabutylammonium fluoride solution in tetrahydrofuran was reacted for 17 hr to provide after workup and purification [one development $CH_2Cl_2$-EtOAc (5:1)]7.5 mg (47%) of the title penem; IR ($CH_2Cl_2$) 3580, 1790, 1710 cm$^{-1}$; NMR ($CDCl_3$)δ1.38 (d,J=6.5 Hz,3H), 1.74 (bd, J=5 Hz, 1H), 3.76 (S,3H), 3.8 (M, 1H), 4.26 (M,1H), 4.76 (M,2H), 5.28 and 5.44 (2M,2H), 5.72 (d,J=1.5Hz, 1H), 5.97 (M,1H), 6.16

(d,J=15Hz,1H), and 7.8 (d, J=15Hz, 1H); UV (dioxane)λ$_{max}$271, 343 nm.

Example 11

Allyl-(5R,6S)-6-[(R)-1-hydroxyethyl]-2-(2-cyanovinyl-thio]-penem-3-carboxylate

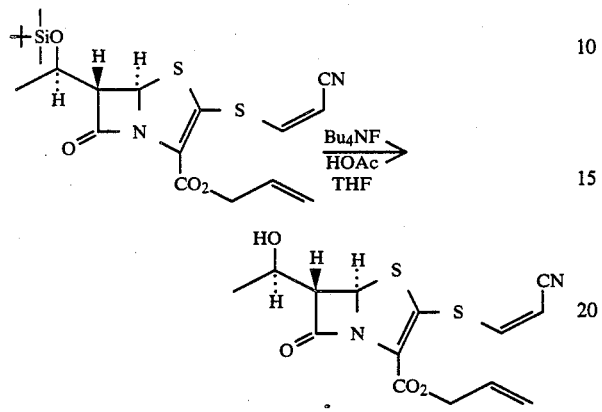

Following the procedure of Example 9, 77.9 mg (0.17 mmol) of penem from Example 2, 148 µL (2.58 mmol) of glacial acetic acid, and 775.5 µL (0.78 mmol) of a 1M solution of tetrabutylammonium fluoride in tetrahydrofuran was reacted for 18 hours to provide after workup and purificaton [one development CH$_2$Cl$_2$-EtOAc (3:1)]31.9 mg (55%) of the title penem; mp. 156°-157.5° C. (Ch$_2$Cl$_2$-pet. ether); [α]$_D$ +421 (c 1, CHCl$_3$); IR (CH$_2$Cl$_2$) 3600, 2238, 1800, 1720, (sh), 1700cm$^{-1}$;NMR (CDCl$_3$)δ 1.38 (d, J=6.5Hz,3H), 1.92 (bd, J=6Hz,1H), 3.82 (dd, J=2 and 7Hz, 1H), 4.29 (M, 1H), 4.79 (m, 2H), 5.31 and 5.46 (2m, 2H), 5.6 (d, J=10Hz, 1H), 5.73 (d, J=2Hz, 1H), 5.96 (m, 1H), and 7.42 (d, J=10Hz, 1H); UV (dioxane)λ$_{max}$269, 325, 345 nm, MS m/e 338 (M$^+$) 253.

Example 12

Allyl-(5R,6S)-6-[(R)-1-hydroxyethyl]-2-([Z-2-carbamoylvinylthio]-penem-3-carboxylate

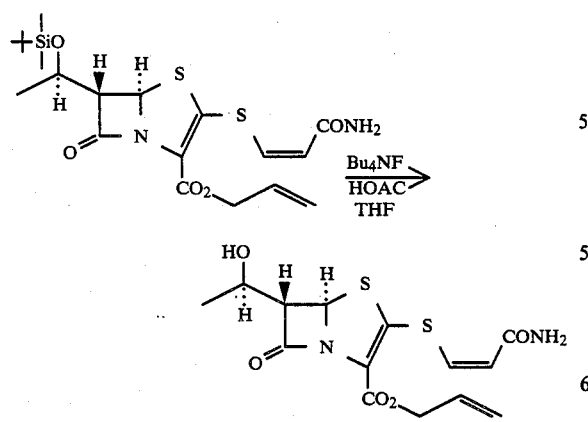

Following the procedure of Example 9, 72.0 mg (0.153 mmmol) of penem from Example 3, 131.5 µL (2.3 mmol) of glacial acetic acid, and 689 µL (0.689 mmol) of a 1M solution of tertrabutylammonium fluoride in tetrahydrofuran was reacted for 20 hr to provide after workup and purfication [one development EtOAc] 39.4 mg (72.3%) of the title penem; [α]$_D$+200.6 (c 1.01, THF); NMR (acetone-d$_6$)δ1.3 (d,J=6.5 Hz, 3H), 3.86 (dd, J=1.5 and 7.0 Hz, 1H), 4.18 (m, 1H), 4.72 (m, 2H), 5.22 and 5.48 (2m, 2H), 5.80 (d, J=1.5 Hz, 1H), 5.98 (m, 1H), 6.26 (d, J=10 Hz, 1H), 6.54 (bs, 1H), 7.12 (bs, 1H), and 7.3 (d, J=10Hz, 1H); UV (dioxane)λ$_{max}$266, 342 nm.

Example 13

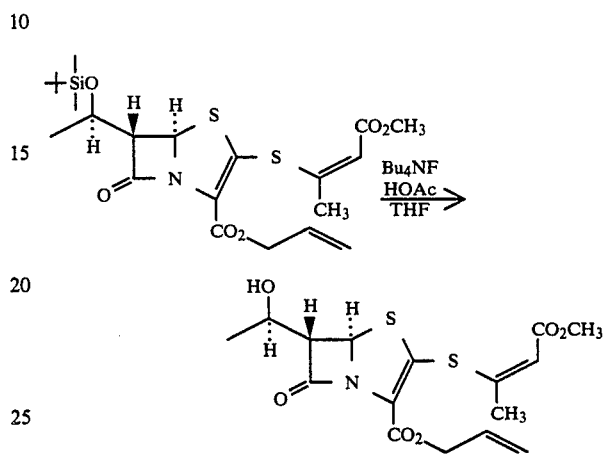

Allyl-(5R,6S)-6-[(R)-1-hydroxyethyl]-b 2-([Z-3-carbomethoxy prop-2-enylthio]-penem-3-carboxylate Following the procedure of Example 9, 31.0 mg (0.062 mmol) of penem from Example 5, 53.3 µL (0.93 mmol) of glacial acetic acid, and 279.5 µL (0.28 mmol) of 1M tetrabutylammonium fluoride in THF was reacted for 19 hour to give after workup and purification [one development CH$_2$Cl$_2$-EtOAc (3:1)]7.0 mg (29%) of the title penem; NMR (CDCl$_3$)δ1.36 (d, J=6.5 Hz, 3H), 1.66 (bs,1H), 2.28 (d, J=1Hz, 3H), 3.74 (s, 3H), 3.84 (dd, J=2 and 7Hz, 1H), 4.28 (m, 1H), 4.74 (m, 2H), 5.26 and 5.42 (2M, 2H), 5.68 (d, J=2Hz, 1H), 5.92 (m, 1H), and 6.04 (q, J=1Hz, 1H); UV (dioxane)λ$_{max}$265, 334 nm; MS m/e 385 (M$^+$), 299, 201.

Example 14

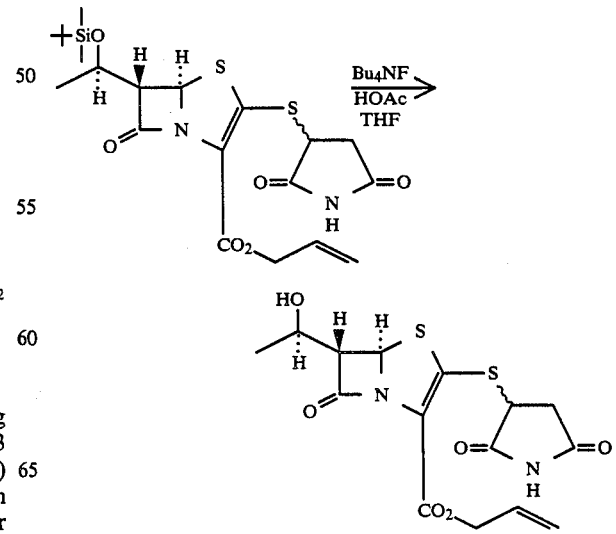

Allyl-(5R,6S)-6-[(R)-1-hydroxyethyl]-2-[(R,S)-3suc-cimidoylthio]-penem-3-carboxylate Following the procedure of Example 9, 39.5 mg (0.079 mmol) of penem from Example 8, 45.4 μL (0.79 mmol) of glacial acetic acid, and 238 μL(0.24 mmol) of 1M tetrabutylammonium fluoride in THF was reacted for 17 hr to give after workup and purification [one development EtOAc-CH2Cl2(2:1)]12.9 mg (42%) of the title penem; IR(CH2Cl2) 3600, 3400, 1795, 1730, 1710 (sh) cm$^{-1}$; NMR (CDCl3)δ1.4 (d, J=6.0 Hz,3H), 2.86 (m, 2H), 3.36 (m, 1H), 3.83 (m, 1H), 4.32 (m, 1H), 4.76 (m, 2H), 5.3 and 5.44 (2M, 2H), 5.71 and 5.75 (2bs, 1H), 5.96 (m, 1H), and 7.87 and 7.91 (2bs, 1H); UV (dioxane λ$_{max}$258, 339 nm; MS m/e 383 (M$^+$-1), 327, 241 98.

EXAMPLE 15

Potassium-(5R,6S)-6-[(R)-1-hydroxyethyl]-2-[(Z-)-2-carbomethoxyvinylthio]- penem-3-carboxylate

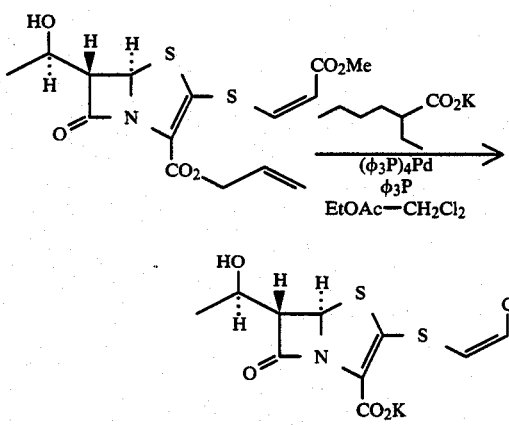

To a stirred solution of 14.5 mg (0.039 mmol) of penem from Example 9 in 0.25 mL CH2Cl2 and 0.5mL EtOAc at ambient temperature in a centrifuge tube was added sequentially 1.0 mg (0.0039 mmol) of triphenylphosphine, 1.4 mg (0.0012 mmol) of tetrakistriphenylphosphinepalladium (0), and 86 μL (0.043 mmol) of 0.5M potassium-2-ethylhexanoate in EtOAc. The resulting mixture was stirred at ambient temperature under at atmosphere of nitrogen for 0.5 hour. The product precipitated from the solution after 4 min. of reaction. The reaction was cooled in an ice-H2O bath, stirred, and 5 mL Et2O added. The separated product was centrifuged and the supernatant decanted. The remaining solid was washed analogously with EtOAc and lastly with Et2, and dried in vacuo. Purification by reverse phase plate layer chromatography in the cold [one development 5% EtOH in H2O]afforded after extraction with MeCN-H2O (4:1), dilution of the extract with H2O, extraction with Hexanes, concentration in vacuo, and lyopholization 8.1 mg of the title penem; NMR(D2O) δ1.32 (d, J=6.5Hz, 3H), 3.8 (S, 3H), 4.02 (dd, J=1.5 and 6.0 Hz, 1H), 4.3 (m, 1H), 5.76 (d, J=1.5 Hz, 1H), 6.11 (d, J=10Hz, 1H), and 7.67 (d, J=10Hz, 1H); UV (H2O) λ$_{max}$327, 272 nm.

Example 16

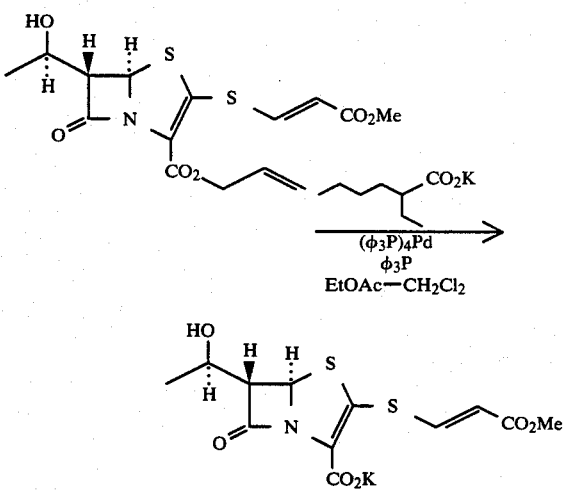

Potassium-(5R,6S)-6-[(R)-1-hydroxyethyl]-2-[(E-)-2-carbomethoxyvinylthio]- penem-3-carboxylate Following the procedure described in Example 15, 7.1 mg (0.019 mmol) of penem from Example 10 in 0.1 mL CH2Cl2 and 0.2 mL EtOAc was reacted with 0.5 mg (0.0019 mmol) triphenylphosphine, 0.7 mg (0.0006 mmol) tetrakistriphenyl-phosphinepalladium (o), and 42 μL(0.021mmol) of 0.5 M potassium-2-ethylhexanoate in EtOAc to give after workup and purification [one development 15% EtOH in H2]3.5 mg (50%) of the title penem; NMR (D2O)δ1.34 (d, J=6.5 Hz, 3H), 3.78 (s,3H), 4.04 (dd, J=1.5 and 6Hz, 1H), 4.3 (m, 1H), 5.8 (d, J=1.5Hz, 1H), 6.26 (d, J=15.5Hz, 1H), and 7.94 (d, J=15.5 Hz, 1H); UV (H2O)λ$_{max}$323, 269 nm.

Example 17

Potassium-(5R,6S)-6-[(R)-1-hydroxyethyl]-2-[(Z)-2-cyanovinylthio]-penem-3-carboxylate

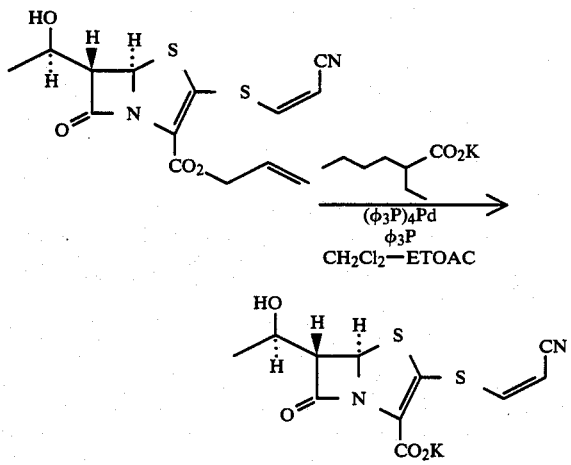

Following the procedure described in Example 15, 31.5 mg (0.093 mmol) of penem from Example 11, 7.3 mg (0.028 mmol) of triphenylphosphine, 5.4 mg (0.0047 mmol) of tetrakistriphenylphosphinepalladium (0), and 186.4 μL (0.093 mmol) of 0.51 M potassium-2-ethylhexanoate in EtOAc was reacted in 3.6 mL of EtOAc -CH2Cl2 (1:1) for 45 minutes to give after workup and purification [one development 15% EtoH in H₂O]18.9 mg (60%) of the title penem; [α]_D+303.5 (c 0.94 H₂O); UV (H₂O)λ_max326, 266 nm; NMR (D₂O)δ1.34 (d, J=6.5 Hz, 3H), 4.04 (dd, J=1.5 and (D₂O) <1.34 (d, J=6.5 Hz, 3H), 4.04 (dd, J=1.5 and 6.0 Hz, 1H), 4.3 (m, 1H), 5.76 (d, J=10.5 Hz, 1H), 5.8 (d, J=1.5 Hz, 1H), and 7.75 (d, J=10.5 Hz, 1H).

Example 18

Potassium-(5R,6S)-6-[(R)-1-hydroxyethyl]-2-[(Z)-2-carbamoylvinylthio]-penem-3-carboxylate

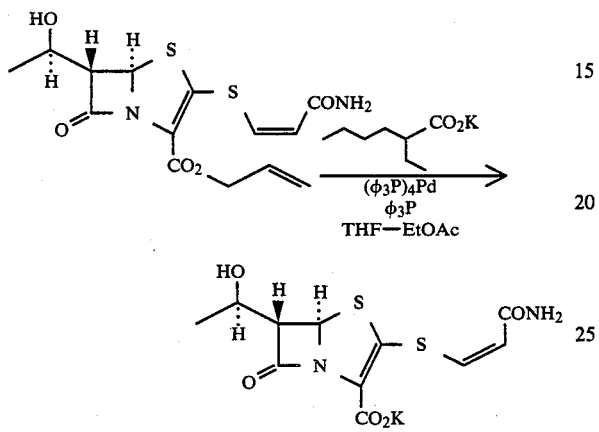

Following the procedure described in Example 15, 34.0mg (0.0955 mmol) of penem from Example 12, 7.5mg (0.0287 mmol) of triphenylphosphine, 4.4 mg (0.0038 mmol) of tetrakistriphenylphosphinepalladium (0), and 191μL (0.0955 mmol) of 0.5M potassium-2-ethylhexanoate in EtOAc was reacted in 3 mL distilled tetrahydrofuran and 0.8 mL EtOAc for 1.0 hour. After this time the product was precipitated from the solution by the addition of 8mL of Et₂O. After the usual workup and purification [one development 10% EtOH in H₂O]- there was obtained 23.9mg (71%) of the title penem; [δ]_D+207.8 (c0.95, H₂O); NMR (D₂O)δ1.33 (d, J=6.5 Hz, 3H), 3.99 (dd, J=1.5 and 6.5 Hz, 1H), 4.28 (p, J=6.5 Hz), 5.74 (d, J=1.5Hz, 1H), 6.18 (d, J=10Hz, 1H), and 7.46 (d, J=10Hz, 1H); UV (H₂O) λ_max327, 268 nm.

Example 19

Potassium-(5R,6S)-6-[(R)-1-hydroxyethyl]-2-[(Z-)-3-carbomethoxyprop-2-enylthio]-penem-3-carboxylate

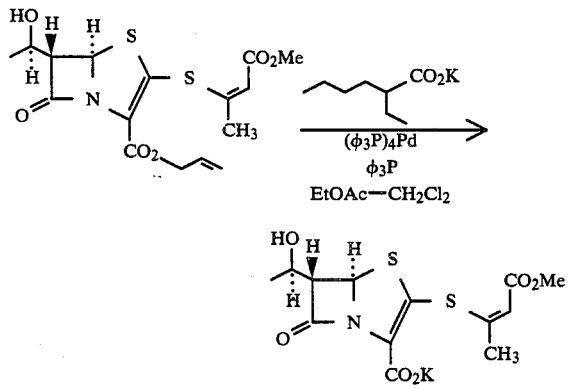

Following the procedure described in Example 15, 7.0 mg (0.018 mmol) of penem from Example 13, 36.4 μL (0.018 mmol) of 0.5 M potassium-2-etylhexanoate in EtOAc, 1.4 mg (0.0055 mmol) of triphenylphosphine, and 1.0 mg (0.0009 mmol) of tetrakistriphenylphosphine-palladium (0) in 0.5 mL CH₂Cl₂-EtOAc (1:1) was reacted from 45 minutes to provide after workukp and puurification [one developement 15% EtOH in H₂O] 4.0 mg (57%) of the title penem; NMR (D₂O)δ1.3 (d, J=6.5 Hz, 3H), 2,34 (d, J=1Hz, 3H), 3.74 (s, 3H), 4.05 (dd, J=1.5 and 6Hz, 1H), 4.28 (m,1H), 5.76 (d, J=1.5 Hz, 1H), and 6.16 (q, J=1Hz, 1H); UV (H₂O) λ_max320, 272 nm.

Example 20

Potassium-(5R,6)-6-[(R)-1-hydroxyethyl]-2-[(R,S)-3-succinimidoylthio]-penem-3-carboxylate

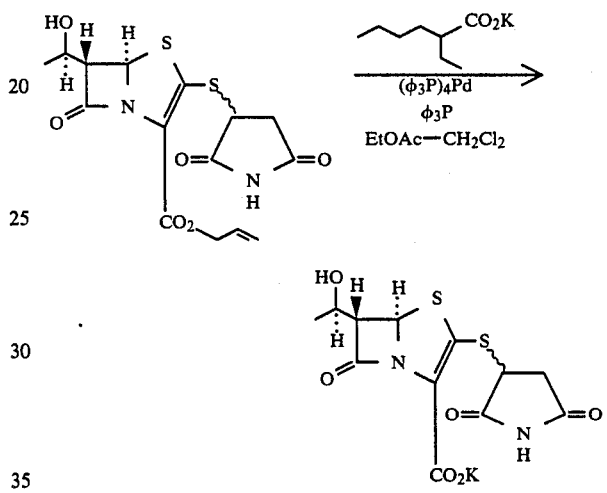

Following the procedure described in Example 15, 12.6mg (0.033 mmol) of penem from Example 14, 1.1 mg (0.001 mmol) of tetrakistriphenylphosphinepalladium (0), 0.9 mg (0.0033 mmol) of triphenylphosphine, and 72.2 μL (0.036 mmol) of 0.5M potassium-2-ethylhexanoate in EtOAc was reacted in 0.3 mL EtOAc and 0.25 mL CH₂Cl₂ for 44 minutes to give after workup and purification 3.1 mg (25%) of the title penem; NMR (D₂O )δ1.3 (d,J=6.5 Hz, 3H), 2.94 (m, 2H), 3.4 (M, 1H), 3.98 (dd, J=1 and 6Hz, 1H), 4.26 (m, 1H), and 5.72 (d, J=1Hz, 1H); UV (H₂O)λ_max 324 nm, 255 nm.

Example 21

Preparation of Pharmaceutical Compositions

One such unit dosage form is prepared by mixing 120 mg of compound A: (Compound of Example 18) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |

| TABLET | PER TABLET |
|---|---|
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water to | 1 ml. |
| OTIC SOLUTION | |
| Compound A | 100 mg. |
| Benzalkonium chloride | 0.1 mg. |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol U.S.P. | 1.0 gram |

What is claimed is
1. A compound having the structure:

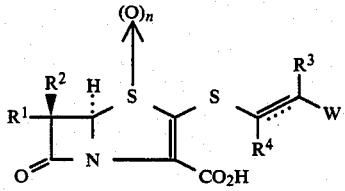

I and the pharmaceutically acceptable salts and esters thereof; wherein $R^1$=CH$_3$CH(OH), $R^2$=H, $R^3$ and $R^4$ are independently selected from: hydrogen; substituted and unsubstituted: alkyl, fluoro, benzyl; phenyl; wherein the substituent or substituents on $R^3$ and $R^4$ are selected from fluoro, hydroxyl, alkoxyl cyano, carboxyl, carbamoyl, amino, and the above recited values for $R^3$ and $R^4$; n is 0 or 1; W is an electron withdrawing group, which is selected from —COR$^5$, CN, and SO$_2$C$_6$H$_5$; wherein $R^5$ is hydrogen; substituted and unsubstituted: alkyl having 1-6 carbon atoms; phenyl cycloalkyl having 3-6 carbon atoms; heteroaryl, heterocyclyl and wherein the heterocyclic ring comprises 4-6 members, one or more being selected from oxygen, nitrogen, and sulfur; or $R^5$ may be: —NR$^7$R$^8$, or —SR$^9$; or substituted and unsubstituted: $R^7$ and $R^8$ are independently selected from: hydrogen, and alkyl having 1-6 carbon atoms; $R^9$ is selected from the same group comprising $R^7$ and $R^8$, but excludes hydrogen; wherein: the substituent or substituents on the above-defined radical groups are selected from: fluoro, hydroxyl, alkoxyl, cyano, carboxyl, carbamoyl, amino, and the above recited values for $R^3$ and $R^4$; $R^3$ may also be W; when the unsaturated moiety attached to the exocyclic sulfur atom is acetylenic (the triple bond exits), then $R^3$ and $R^4$ are nonexistent and W is as previously defined.

2. A compound according to claim 1 selected from the group consisting of:

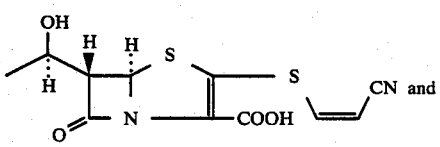

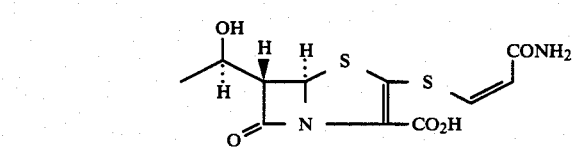

3. A compound of claim 1 wherein the species is represented as its pharmaceutically acceptable sodium or potassium carboxylic acid salt or ester.

4. An antibacterial pharmaceutical composition comprising a therapeutically effective amount of a compound of claim 1 and a pharmaceutically acceptable carrier therefor.

5. An antibacterial method of treatment comprising administering a therapeutically effective amount of a compound of claim 1.

* * * * *